United States Patent
Schmitz et al.

(10) Patent No.: US 7,452,511 B2
(45) Date of Patent: Nov. 18, 2008

(54) REACTOR FOR PRODUCTION OF CHLORINE DIOXIDE, METHODS OF PRODUCTION OF SAME, AND RELATED SYSTEMS AND METHODS OF USING THE REACTOR

(76) Inventors: Wilfried J. Schmitz, 10387 Autumn Valley Rd., Jacksonville, FL (US) 32257; David Francis, 921 Lotus La., Jacksonville, FL (US) 32259

( * ) Notice: Subject to any disclaimer, the term of this patent is extended or adjusted under 35 U.S.C. 154(b) by 506 days.

(21) Appl. No.: 10/430,360

(22) Filed: May 5, 2003

(65) Prior Publication Data
US 2005/0244328 A1   Nov. 3, 2005

Related U.S. Application Data

(60) Provisional application No. 60/377,397, filed on May 3, 2002.

(51) Int. Cl.
*B01J 19/00*   (2006.01)
*C01B 11/02*   (2006.01)

(52) U.S. Cl. .................. 422/129; 422/111; 422/112; 422/202; 422/240; 422/242; 423/477

(58) Field of Classification Search .............. None
See application file for complete search history.

(56) References Cited

U.S. PATENT DOCUMENTS

| | | | |
|---|---|---|---|
| 4,251,224 A | | 2/1981 | Cowley et al. |
| 4,414,193 A | * | 11/1983 | Fredette et al. .............. 423/478 |
| 4,534,952 A | * | 8/1985 | Rapson et al. .............. 423/478 |
| 4,945,992 A | * | 8/1990 | Sacco .......................... 166/310 |
| 5,227,306 A | * | 7/1993 | Eltomi et al. ................. 436/55 |
| 5,324,497 A | | 6/1994 | Westerlund |
| 5,458,858 A | | 10/1995 | Dawkins |
| 5,565,182 A | | 10/1996 | Sokol |
| 6,235,240 B1 | | 5/2001 | Heredia et al. |
| 6,716,354 B2 | * | 4/2004 | Rosenblatt et al. .......... 210/638 |
| 6,967,010 B2 | * | 11/2005 | Cowley et al. .............. 422/305 |

FOREIGN PATENT DOCUMENTS

| | | | |
|---|---|---|---|
| CA | 2337599 A1 | * | 8/2001 |
| DE | 3723799 A1 | * | 1/1989 |

* cited by examiner

*Primary Examiner*—Jennifer A Leung
(74) *Attorney, Agent, or Firm*—Timothy H. Van Dyke; Beusse Wolter Sanks Mora & Maire

(57) ABSTRACT

A novel chlorine dioxide production apparatus, or reactor, is disclosed. The reactor receives reactants from two or more feed pipes under pressure, and the reactants react in a reaction chamber that operates under elevated pressure and within a specified temperature range. A gaseous product, such as chlorine dioxide, is generated and is released directly into a liquid stream for bleaching, disinfection, and other purposes. Also disclosed is a novel system for production of quantities of chlorine compounds from commercial grades of starting materials, and methods of using the reactor in situ for bleaching, and for disinfection, decontamination, and sterilization of flows of water or other liquids. An automated system for multiple points of addition of chlorine dioxide to a flow to be treated is also disclosed.

24 Claims, 11 Drawing Sheets

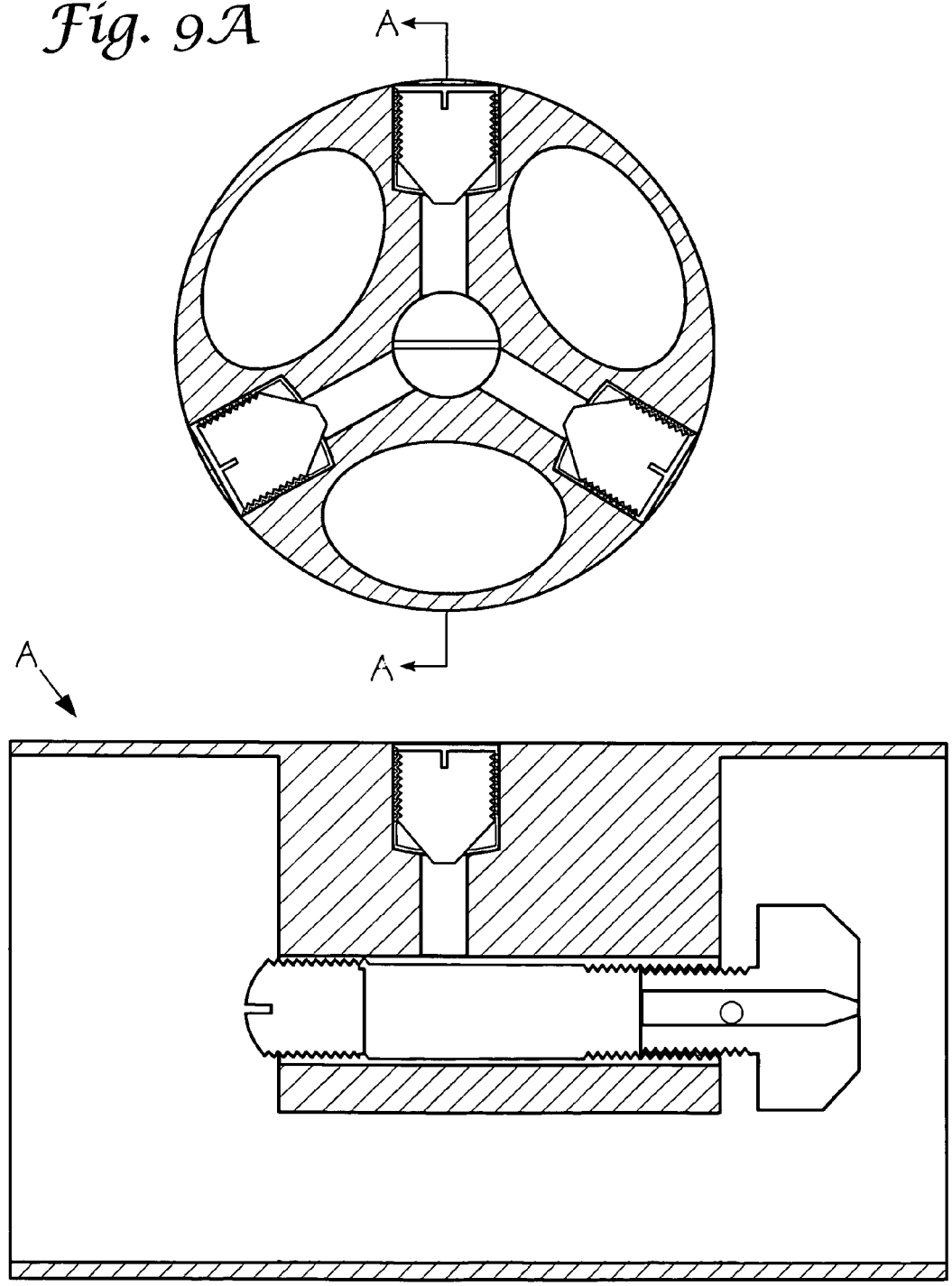

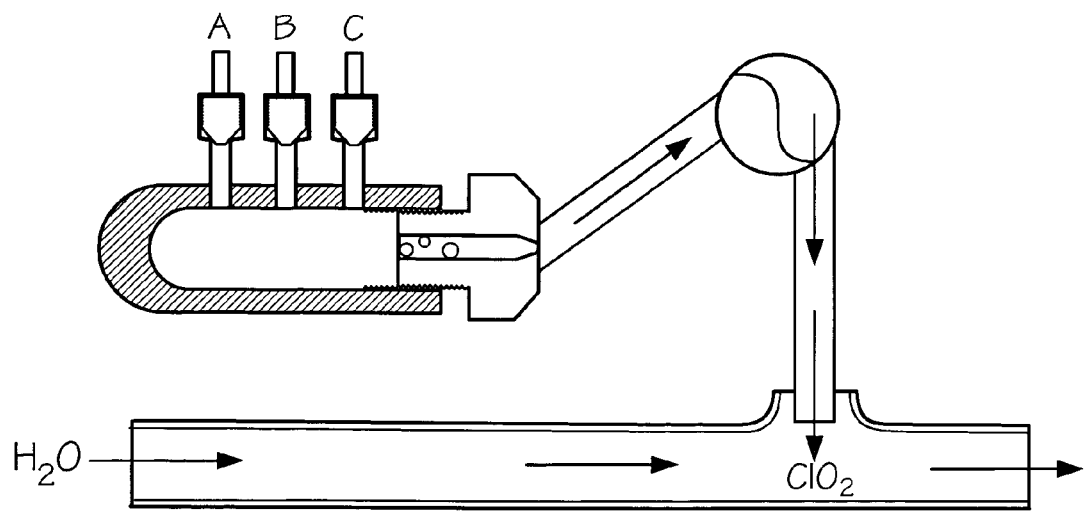
Fig. 10
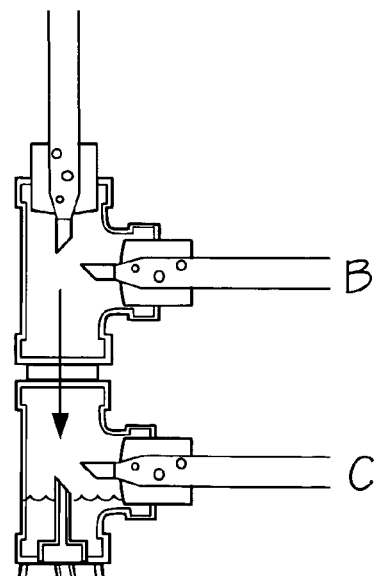
Fig. 11

REACTOR FOR PRODUCTION OF CHLORINE DIOXIDE, METHODS OF PRODUCTION OF SAME, AND RELATED SYSTEMS AND METHODS OF USING THE REACTOR

FIELD OF THE INVENTION

The present invention relates to a novel chlorine dioxide production apparatus, or reactor, to a novel system for production of quantities of chlorine dioxide from commercial and other grades of starting materials, and to methods of using the reactor in situ, for example within a pipe containing a liquid, or separately from that pipe but air-cooled or water-cooled as needed, for bleaching, and for disinfection, decontamination, and sterilization of flows of water or other liquids.

BACKGROUND OF THE INVENTION

Various species of chlorine are used in small- and large-scale bleaching, oxidation, and disinfection operations. These operations range from providing a weak sodium hypochlorite solution in a bottle for household whitening and disinfection (liquid bleach solutions, about 5% sodium hypochlorite), to delivering pure chlorine gas to a wastewater treatment plant waste stream. One problem with the use of pure chlorine gas, however, is its high toxicity and risk to workers case of leaks and accidents.

A common approach for large-scale water purification that can be safer than the transportation and subsequent on-site use of chlorine gas is the on-site production of chlorine dioxide. This strong oxidant is used for oxidation to disinfect water flows in drinking water treatment plants and in wastewater treatment plants. As a strong oxidant, chlorine dioxide destroys viruses, bacteria, and other microscopic organisms as it oxidizes compounds having a lower oxidation potential than itself. To maximize its oxidation and disinfection effects, in a water treatment system chlorine dioxide is preferably added after the sedimentation tank or basin.

Chlorine dioxide (ClO2; CASR n 10049-04-4) is a greenish-yellow gas at room temperature that is stable in the dark but unstable in the light. As noted, it is recognized as an extremely powerful biocide, disinfectant agent and oxidizer. As to regulatory allowance of chlorine dioxide in commercial and wastewater and water purification applications, in 1967, the United States Environmental Protection Agency ("EPA") first registered the liquid form of chlorine dioxide for use as a disinfectant and sanitizer. In 1988, EPA registered chlorine dioxide gas as a sterilant.

Chlorine dioxide kills microorganisms by disrupting transport of nutrients across the cell wall. Chlorine dioxide can be generated in a gas or liquid form and smells like chlorine bleach. However, chlorine dioxide is not to be confused with chlorine gas. They are two distinct chemicals that react differently and produce by-products that also have little in common.

Chlorine dioxide, $ClO_2$, offers the following benefits. First, $ClO_2$ functions via an oxidative rather than chlorinating reaction, the mode of action of chlorine gas. This virtually eliminates the formation of chlorinated organic compounds that are suspected to increase certain cancer risks. Second, $ClO_2$ when generated on site, eliminates the need for site storage of chlorine and/or transportation thereof.

Several types of chlorine dioxide generators are commercially available. Many still utilize gaseous chlorine in their generation process, and while effective, the risk management issues associated with chlorine still remain. Embodiments of the present invention do not use chlorine gas as a reactant. As a result, there is less risk of harm in use of embodiments of the present invention. Further, it is noted that chlorine dioxide gas, is unstable and explosive at pressures over about 40 kPA. Thus the gas form is not routinely safely transported, and instead is produced at the site of use. One system, described in U.S. Pat. No. 6,325,970B1, issued Dec. 4, 2001, uses an in-line system that combines a chlorite, a chlorine donor, and an acid in an in-line system in which chlorine dioxide is formed and introduced directly into a water flow. A typical solution taught by U.S. Pat. No. 6,325,970B1 is a mixture comprising about 10 percent of a 28 percent sodium chlorite solution, about 10 percent of a 12 percent sodium hypochlorite solution, about 1.5 percent of a sodium hydroxide solution, and about 80 percent water. To generate chlorine dioxide, acid is added; the release of chlorine dioxide is stated to be faster with stronger acid solutions. It is stated that the molar ratios of the chlorite and chlorine donor are set such that substantially no gaseous chlorine dioxide is formed. It appears another factor is the relatively low concentrations of the reactants, and the overall reaction conditions. While this approach provides a margin of safety by avoiding the generation of gaseous chlorine dioxide, it is limited to producing relatively low concentrations of chlorine dioxide. For instance, it is stated that a preferred embodiment yields 20,000 to 50,000 parts per million (ppm) of chlorine dioxide before dilution. This is less than five-percent active chlorine, which is very dilute for industrial and municipal bleaching and disinfection operations, respectively.

In addition to U.S. Pat. No. 6,325,970B1, many other approaches are known in the art to produce chlorine dioxide from relatively pure metal chlorite salts, such as magnesium, calcium or sodium chlorites, that are reacted with an acid and/or a chlorine donor. Such approaches may provide yields of chlorine dioxide that range, for instance, from 60 to 98 percent. However, many of the published or patented methods are based on experimentation using, or assuming, high purity (near 100%) of the chlorite or chlorate reactants. Often, when such methods are used with lower purity technical or commercial grades of reactants, the stated yields are considerably lower than the yields stated in such papers and patents. Also, the range of undesired by-products of reactions using the lower purity technical or commercial grades can be greater, and the concentrations of such undesired by-products can be unacceptably high for certain disinfection applications.

Further, it is noted that U.S. Pat. No. 5,061,471 (issued Oct. 29, 1991 to Sundblad and Lovetro), and their prior published application, EPO 88850011.3, disclose a process for continuous production of chlorine dioxide in a cooled reaction vessel subjected to "overpressure." In contrast to the present invention, the '471 patent discloses a different set of reactants, namely, combining aqueous solutions of an alkali metal chlorate, sulfuric acid, and bubbling in gaseous sulfur dioxide (or, alternately, adding liquid sulfur dioxide). Also, the reaction chamber includes a coil through which a cooling liquid may be passed. It is stated that one advantage of the use of sulfur dioxide is that it reduces chlorine in the reaction vessel.

Many references disclose methods of production of chlorine dioxide. However, these references have not achieved the reliable results and consistent operation of the present invention, using the reactants and conditions of the present invention.

Another aspect of certain embodiments of the present invention is the addition of longer-surviving disinfectant species in combination with chlorine dioxide, for certain applications. Despite its basic effectiveness as an oxidant and disinfectant, chlorine dioxide alone may not provide sufficient disinfection over a sufficiently long time and distance in pipes compared to other chlorine species. There are reports of odor and/or taste issues when using chlorine dioxide as the only chlorine species in a water treatment plant. A possible solution is to add or to co-generate chloramines, which are typically produced as by-products of chlorine gas disinfection, and which are known to have longer term effect as residual chlorine species. With chloramine acting as a secondary disinfectant and chlorine dioxide serving as the primary disinfectant, more effective disinfection and reliable odor and taste removal are achievable.

Given the toxicity and risk inherent in the use of chlorine gas, there is a need to develop a safer and reliable alternative to its use in oxidation and disinfection applications. Given the overestimates of yields and understatement of by-products by known methods of chlorine dioxide production when technical or commercial grades of starting materials are used, there is a need to develop a method that reliably and consistently can utilize technical and commercial grades of chlorine reactants to produce chlorine dioxide at sufficiently high, economical yields with a minimum of undesirable by-products. Finally, given the need in some applications to add chloramines as secondary disinfectants when chlorine dioxide is used as the primary disinfectant, there is a need, at least for some applications, to have an effective means to add or produce a given quantity and type of chloramines in a disinfection system or process.

It also is noted that given updated regulations for EPA Class I wastewater treatment plant effluents, as stated in recent disinfectant byproducts rules that mandate lower levels of trihalomethanes and haloacetic acids, it is expected that the substitution of chlorine dioxide for chlorine disinfection will be favored in order to meet these new rules and related standards. Under such a regulatory environment, the present invention is expected to find many applications in new Class I wastewater treatment plants.

Finally, although chlorine dioxide delivered in solution is relatively safer than chlorine gas, the gas form is more toxic and dangerous. However, because the economics of production favor the generation of the gas, there is a need to develop a system using chlorine dioxide gas in which the chance of leakage or exposure is minimized.

Five references that provide relevant background information about disinfection and chlorine dioxide are "Guidelines for Drinking-Water Quality", $2^{nd}$ Edition, World Health Organization, Geneva, "The Chlorine Dioxide Handbook," by Donald J. Gates, June 1998, AWWA, published as part of the Water Disinfection Series, ANSI/NSF Guideline 61, Weast, R. C., "CRC Handbook of Chemistry and Physics", 52nd edition, p. D-105, 1971 (no month), and W. J. Masschelein's basic textbook entitled: "Chlorine Dioxide. Chemistry and Environmental Impact of Oxychlorine Compounds", pp. 112 to 145. 1979 (no month). These references, and all patents and other references cited in this disclosure, and hereby incorporated by reference into this disclosure.

The present invention, described and claimed below, advances the art by providing a reaction chamber, a system, and methods for the production of chlorine dioxide gas for oxidation and disinfection purposes. As described below, it advances the art by meeting the needs stated immediately above.

SUMMARY OF THE INVENTION

The present invention relates to a novel reaction chamber useful in the high-yield production of chlorine dioxide gas from commercial and technical grade reactants. The present invention also is directed to a process of generating chlorine dioxide gas in the novel reaction chamber, or reactor, which preferably includes operating the reactor at specified elevated pressure and/or temperature. The invention also includes systems useful for the addition of chlorine dioxide to flows in need of such compound in which more than one point of addition is provided, and monitoring of more than one point along the flow provides for replenishment of chlorine dioxide at points after the initial point of addition.

Thus, one object of the present invention is to advance the art of chlorine dioxide generation with a new design of a reaction chamber in which commercial and technical grades of common reactants are driven to react to completion or near completion to generate high yields of chlorine dioxide gas. A related object is to have the reaction chamber with an adjustable volume, which in certain embodiments permits adjustment of the chamber volume to correlate with the relative production levels of chlorine dioxide required in a particular application of the chamber. This permits a single chamber to function to produce chlorine dioxide across a wider range of outputs.

Another object of the present invention is to practice a method of chlorine dioxide production which involves reacting commonly available commercial and technical grade reactants under pressure and within a specified temperature range to generate high yields of chlorine dioxide gas. Another object of the invention is to use the same reactor to produce oxidant species other than chlorine dioxide by using the reactor system at elevated pressure and at a selected temperature range to drive other compounds to yield desired strongly oxidizing species.

Another object of the present invention is to provide a means to produce chlorine dioxide in a place close to its use for disinfection of a stream of water or other liquid, to reduce the risks of toxics release and harm to workers, the environment, and nearby persons.

Another object of the present invention is to advance the art of production of chlorine dioxide through its production at elevated temperature and pressure by combining a chlorite source, for instance sodium chlorite solution, with an acid source, such as sodium bisulfate, and optionally also adding a halogen donor, such as sodium hypochlorite.

The foregoing has outlined some of the more pertinent objectives of the present invention. These objectives should be construed to be merely illustrative of some of the more prominent features and applications of the invention. The following detailed description and embodiments are exemplary and explanatory only and are not to be viewed as being restrictive of the present, as claimed. These and other objects, features and advantages of the present invention will become apparent after a review of the entire detailed description, the disclosed embodiments, and the appended claims. As will be appreciated by one of ordinary skill in the art, many other beneficial results and applications can be attained by applying modifications to the invention as disclosed. Such modifications are within the scope of the claims appended hereto.

DESCRIPTION OF THE DRAWINGS

FIG. 9A is a cross-sectional view of an embodiment of the reactor of the present invention. This reactor embodiment is machined from a CPVC or other appropriately chemically resistant plastic block, providing three channels through which water flows, cooling the reaction chamber. The chemical injection points are through three bored chemical feed entrances positioned at 120 degrees relative to each other. The chemicals directly impinge and mix at a central point. Also, spaces for check valves are provided in this single piece, and check valves are placed therein.

FIG. 10 is a diagrammatic view of an embodiment of the present invention which uses a positive-displacement pump to draw the reactants into a reaction chamber of the present invention. The reactants mix, react, and the end-products, largely chlorine dioxide gas, are pumped out by the same pump.

FIG. 11 is a diagrammatic view of an embodiment of the present invention which utilizes commercially available CPVC pipe fittings to form a reactor of the present invention. In this embodiment, a standpipe is at the gravitational bottom of the reactor so constructed, providing for a pooling or mixing effect at the bottom of the reaction chamber. As chemical reactant liquids are pumped into the chamber, they accumulate or pool at the bottom, react, form chlorine dioxide which is in gas and solution form. Gas and liquid from this chamber are expelled through the opening of the standpipe, and go therefrom into the stream of the water to be disinfected.

DESCRIPTION OF THE PREFERRED EMBODIMENTS

Figure 1:
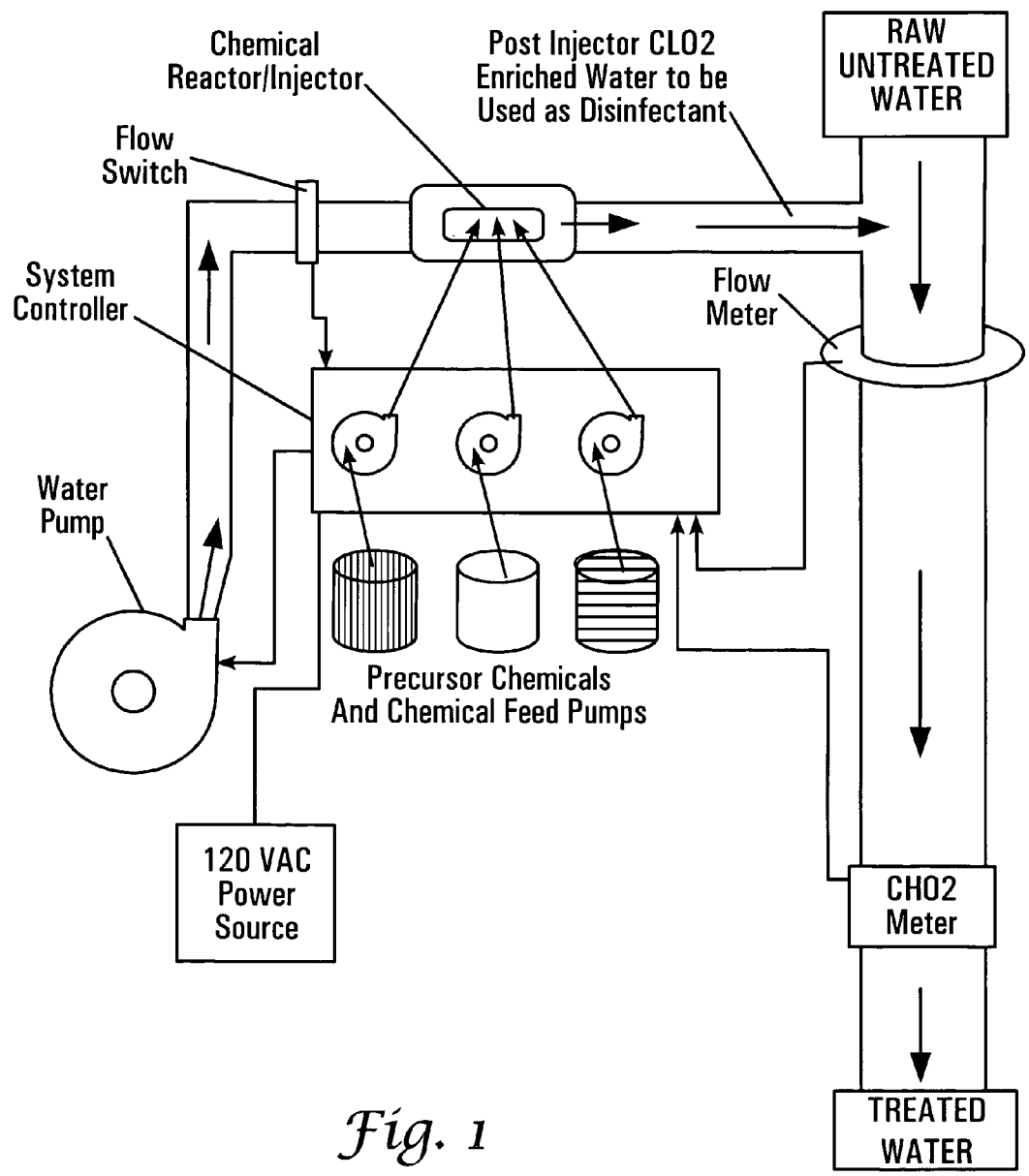
FIG. 1 presents a generalized depiction (not to scale) of a water system to which an embodiment of the chlorine dioxide system of the present invention.

One aspect of the present invention is a novel reactor, having as a key component a reaction chamber, which are engineered to optimize the production of chlorine dioxide gas from reactions among various combinations of reactants. As used throughout this disclosure, the terms reactants, pre-cursor chemicals, pre-cursor materials, and starting materials are defined to mean the same thing, namely, the chemicals that are passed into the reaction chamber for reaction to form the one or more products, or end-products, of the reaction. Also as used throughout this invention, pipe has its normal meaning, and "flow channel" is taken to mean a pipe as well as any open channel through which a fluid passes.

Typical embodiments of the chlorine dioxide system of the present invention utilize an acidified chlorite solution with the addition of an additional halogen to hasten the chlorine dioxide generation process. When implemented, for example, to treat a stream of municipal residential or mixed wastewater, this system utilizes a raw water pump to supply the water (carrier media) to an in-situ chemical reactor (also referred to as a reaction chamber or generator). The carrier water pump runs once the system is powered up and wastewater is flowing through the main wastewater conduit (pipe, channel, etc) of the waste stream that is being treated. Preferably, input data from a $ClO_2$ monitor and the flow switch signal the system controller to drive the chemical feed pumps. The chemical feed pumps draw their individual chemical solutions up from their storage tanks and deliver them to the chemical reactor. In preferred embodiments, this reactor is located within the flow of the water supplied by the raw water pump. This is done as a safety feature to assure that the chlorine dioxide goes into immediate solution preventing any potentially explosive conditions from occurring. A flow switch in the raw carrier water line has the function of halting the chemical feed, hence stopping $ClO_2$ generation, should a loss of carrier water occur. It should also be noted that as the reactor is positioned within the carrier water stream any potential leaks or feed line ruptures will not allow escape of the chemicals beyond the contained feed water piping system and not to the atmosphere. In preferred embodiments, each of the chemical feed lines is equipped with a flow switch connected in series with the other flows' flow switches, so that if one flow is interrupted, all flows cease.

As the three chemicals are introduced into the reactor, they react to form $ClO_2$ that, because of the resulting pressure, unseats a check valve and discharges $ClO_2$ into the water stream. Then, this $ClO_2$-enriched water stream flows into the main stream of wastewater as a disinfectant/oxidant solution.

A ClO$_2$ monitor downstream in the system monitors the levels of the chemical and signals the system controller to increase or decrease the flow from the pumps to maintain the desired residual level of ClO$_2$.

The above describes operation of typical embodiments of the chlorine dioxide system of the present invention. Additional safeguards that may be incorporated into these or other embodiments include, but are not limited to: (1) high, low, and critically low level indicators on the chemical storage tanks, (2) check and foot valves on either side of the chemical feed pumps as well as chemical flow switches to assure that all three reactants are supplied to the reactor equally, (3) calibration columns on the discharge side of the chemical feed pumps, (4) check valves and a bypass arrangement around the reactor/injector to allow for service and inspection and (5) bi-directional telemetry to relay signals of the above and/or other parameters to a remote location, and to send back commands to pumps, etc. (such as for control, decision-making), and numerous other features that add to the performance of the system. Such additional features add to system reliability and safety in typical industrial workplace environments.

FIG. 1 provides a general operational diagram of a portion of a wastewater treatment (not to scale) that shows the reactor of the present invention positioned in a wastestream. In FIGS. 2-11, only the reactor is shown; however, it is to be understood that the necessary supplies (i.e., from tanks such as shown in FIG. 1) are connected appropriately to such reactors.

Further, while not being bound to a particular theory, one likely reaction sequence that occurs in the reaction, reactors and systems of the present invention is shown below:

$$NaOCl + NaHSO_4 \rightarrow HOCl + Na_2SO_4 \quad (I)$$

$$HOCl + H \rightarrow \tfrac{1}{2}Cl_2 + H_2O \quad (II)$$

$$NaClO_2 + \tfrac{1}{2}Cl_2 \rightarrow NaCl + ClO_2 \quad (III)$$

Per reaction I, the hypochlorite reacts with sodium bisulfate to produce hypochlorus acid. Per reaction II, the hypochlorus acid so formed in reaction I reacts with additional free hydrogen ion to produce chlorine gas in solution. The excess free hydrogen ion is a result of the acidic reaction condition in the reaction chamber. Then, in reaction III, the chlorine gas reacts with the sodium chlorite to produce chlorine dioxide. The chlorine dioxide gas, given the pressure in the reaction chamber, flows out through a pressure relief valve or other suitable orifice that allows maintenance of the desired pressure in the reaction chamber. Once in the stream of water outside the chamber, the chlorine dioxide gas dissolves in the water. Partial reaction products and reaction byproducts also exit the reactor chamber via this route, or, alternately, are removed via a passage toward the gravitational bottom of the reaction vessel.

In more general terms than the above examples of reactants, as used herein the term "acidifying reactant" is used to mean and include sodium bisulfate, urea sulfate and an organic acid or a blend of two or more organic acids which, when provided to said reaction chamber, reacts with other components therein, including the aqueous media and hydrogen ions, to form or remain an acid, and thereby to maintain a desired low pH in the reaction chamber. While a preferred acidifying reactant is sodium bisulfate, and this compound is used in the examples provided below, this is not meant to be limiting in the broader scope of the invention, and of the claims in which the term "acidifying reactant" is used. The general accepted definition of an organic acid, namely, an acid that contains a carboxy, —COOH, group, is used in defining an acidifying reactant. Organic acids include, but are not limited to: acetic acid; glacial acetic acid; citric acid; lactic acid; and malic acid.

Further, it is noted that some inorganic acids, such as hydrochloric acid, may be used in place of the acidifying reactant as defined above, in the present invention. However, it has been observed that when such inorganic acid is used, the reaction is less stable. While not being bound to a particular theory, one reason for this may be related to the fact that the sulfate group of sodium bisulfate acts as a diprotic acid, while hydrochloric acid is a monoprotic acid. Thus, the use of an inorganic acid that does not fall within the above definition of "acidifying reactant" is not preferred. Also, at least with regard to hydrochloric acid, this acid is more dangerous to handle and more expensive than sodium bisulfate.

By the term "effective amount" is meant an quantity in relation to other additions that has been found, or is determinable without undue experimentation, to be a sufficient amount to achieve a stated purpose, reaction, or goal.

In typical operations of the reactors of the present invention, the following chemical reactant solutions are used. Shown below are the chemical names and the typical concentration ranges for each reactant:

Sodium Bisulfate (~sodium acid sulfate): Typically used at 5% to 33% concentration of graduals to water by weight.

Sodium Chlorite: Typically used at 2% to 40% of granules to water by weight. It is noted, however, that only 80% of technical grade sodium chlorite is available as sodium chlorite. That is, technical grade sodium chlorite contains about 80 percent sodium chlorite, about five percent $Na_2CO_3$, about two percent $NaClO_3$, and about 13% NaCl.

Sodium hypochlorite: 3% to 15% available chlorine concentrations.

More generally, the sodium bisulfate is an example of an acid source for the reaction, the sodium chlorite is an example of a chlorite source/donor for the reaction, and the sodium hypochlorite is an example of a halogen donor for the reaction. As noted herein, the latter is an optional, preferred reactant. Also as noted herein, various substitutions by other chemicals can be made.

Other acids can be used can be used but it has been found that sodium bisulfate results in giving better overall yields and it is economically viable product, when used in the injector.

It is noted that phosphoric acid, hydrochloric acid and citric acid are some of the other acids use in the generation of CLO2. However, the yields are not as high as using the sodium bisulfate, nor is the operation as predictable, and given the low pH of the system using sodium bisulfate, it has been found that most of the chlorite is converted to chlorine dioxide.

Any halogen donor can be used as a replacement to hypochlorite acid, but it has been found that the hypochlorite is more economic, to use and readily available.

Also, it has been observed that when an operation has a flow subject to fluctuating and variable flow rates and that the demand for CLO2 is low, it is better to operate in a pulse mode. Where the demand is high and with higher flow rates it is best to use continuous mode.

As noted elsewhere herein, the injector with the occasional clean out mode, removes the scaling that is formed by calcium deposits when using calcium hypochlorite as the halogen donor.

It also is noted, for the invention in general, that the system and reaction vessel may be operated either in a continuous mode, or in a pulse mode.

The general operating parameters of a typical reaction and reactor are as follows. As to pressure, when the reactor is "in situ" (within a pipe that is carrying water into which the reactor releases the reaction products), the input flow rate of the reactants, the reaction chamber volume, and the outflow from the reactor (typically a nozzle that opens via a pressure relief valve) are adjusted so that the chamber attains a pressure at least greater than the ambient pressure of the liquid in the pipe surrounding the reactor. In this way the reaction products (i.e., chlorine dioxide gas, minerals in solution or expelled as a diluted slurry, chlorine dioxide dissolved within the aqueous phase that largely is comprised of the combined water component of the chemical reactant solutions) are readily released into that stream of liquid on a desired continuous, semi-continuous, or pulsed basis. For instance, it has been found that, for some systems, a pressure relief valve on the reactor set to 65 p.s.i. works suitably, and is greater than the pressure in the ambient wastewater flowing around the reactor. However, it also has been observed, at least in one embodiment, that a suction pump has been effective in drawing the reactants into the reaction chamber, and pumping the products from the reaction chamber into a stream of liquid to be treated, without the requirement for an absolute positive pressure developed in the reaction vessel. Thus, in at least one non-in-situ application of the present invention, a positive pressure in the reaction chamber is not an absolute requirement.

In general, there are several operational alternatives in the use and admixing of the aqueous chemical solutions that contain the reactants of the present invention's method for the production of chlorine dioxide. At a very general level, with regard to pumping simplicity and maintaining a desired ration of reactants to one another, one alternative is to procure or to prepare aqueous chemical solutions at concentrations such that pumping these at 1:1 (where a halogen donor is not added), or 1:1:1 (where a chlorite source, an acidifying chemical, and a halogen source are added) ratios. These solutions are then added at this simple ratio to generate chlorine dioxide. When pumping is used, this provides a benefit in that a single positive displacement pump is capable of providing all three chemical solutions to a desired container for the reaction to produce chlorine dioxide. This also simplifies the adjustment of chlorine dioxide production when such production is being controlled by a feedback loop system—a signal to a single pump adjusts the levels of all two or three chemical reactants. Also, the system is less likely to operate out of the desired range of chemical reactant ratios, as may occur when each chemical reactant is supplied to the reaction container and one pump fails or deviates from its pre-set or pre-calibrated flow rate.

It is recognized that some users may not have an appropriate level of knowledge and/or skill, and/or may not devote the needed time to make adjustments to obtain consistently an output of chlorine dioxide within a desired range. Accordingly, in such situations, as another example of the above alternative, the ratio of the final reactant solutions are maintained at 1:1 or at 1:1:1, but the concentration of the chlorite source is lowered. For instance, not to be limiting, where sodium hypochlorite is the halogen donor, sodium bisulfate is the acidifying reactant, and sodium chlorite is the chlorite source, a stock solution of about 31.25 percent sodium chlorite (nominal strength) is diluted to about five percent (i.e., a 6.25-fold dilution). A stock solution of 30% (nominal strength) of sodium bisulfate is used without dilution, and a 12% (nominal strength) stock solution of sodium hypochlorite is used without dilution. By so diluting the chlorite source, the output of chlorine dioxide is limited, even when the operator raises the pumping rate of the common chemical feed pump to its maximum capacity.

A disadvantage to the above method is that dilution of one or more chemical reactants to adjust to the desired 1:1 or 1:1:1 mixing ratio results in having a larger than needed volume of that adjusted aqueous chemical reactant solution. This may be problematic at certain facilities. Thus, another operational alternative is to obtain chemical reactants at a concentration that is determined suitable for the expected pumping rates (which is determined partly on the available pumps, their accuracy, and the expected demand of chlorine dioxide from the process), and then pump such suitable concentrations separately, at ratios other than 1:1 or 1:1:1.

For instance, in some alternatives, an option is to monitor flow rate cessation by each chemical reactant solution pump, and shut down the entire system shut down if one fails. Another control mechanism is to have a control feedback loop that adjusts the pumping rate of one or more pumps based on a parameter of the system being out of a desired range.

Also, it has been observed that the actual concentration of the halogen donor, when sodium hypochlorite is the halogen donor, may vary and not adversely affect the output of the method. For instance, it is recognized that sodium hypochlorite is unstable and a 12 percent nominal strength stock solution tends to test at a lower actual concentration over time. However, at a pumping ratio of 1:1:1, it has been established that even when the actual sodium hypochlorite concentration of the 12 percent nominal strength stock solution drops to as little as 2.5 percent, a reaction still proceeds favorably when this is mixed at the 1:1:1 ratio with 30% (nominal strength) sodium bisulfate and 31.25 percent (nominal strength) sodium chlorite.

As to pH, a preferred range of the chemical mixture in the reaction chamber during normal operation is from about pH=0.16 to about 4.0 pH units. A more preferred range is from about pH=1.0 to about 3.0 pH units, and a more preferred range is from about 1.5 to about 2.5 pH units. The most preferred pH range, particularly for continuous operation reactors is from about 2.0 to about 2.5 pH units. It is noted that for semi-continuous and pulse reactor regimes, the pH fluctuates as the acidifying reactant enters and reacts in the chamber. Also, it has been observed that, when all other parameters are held constant, an increase in the volume of the reaction chamber results in an increase in pH of the chemical mixture in the reaction chamber.

As to temperature, a preferred range of operating temperature is between about 40 degrees Fahrenheit and about 155 degrees F. A more preferred range is from about 60 to 120 degrees F., a more preferred range is from about 60 to 100 degrees F., and the most preferred temperature range is from about 80 to about 90 degrees F. Further, it is noted that sodium bisulfate stock solution should be maintained at or above about 45 degrees Fahrenheit. This has been found to prevent precipitation of salts, and eliminates crystallization in the stock solution storage container and in the feed lines.

It is noted that the reactants may at times yield a build-up of calcium or other metals within the reactor. This may be caused where the water to be treated contains high levels of calcium and/or other metals, such as iron. These metals may precipitate out and build up as scale within the reactor. Thus, as may be utilized in any of the embodiments of the reactor of the present invention, an additional input, or feed line is introduced into the reactor. This allows for a chemical flushing of the reactor. Such flushing is done with an acid such as the bi-sulfate used in the reaction process. The frequency of the flushing is dependent upon the levels of precipitants in solution.

Also, it is noted that the use of sodium bisulfate in the production of chlorine dioxide is unexpected, as sodium bisulfate is known to be useful in the reduction and removal of chlorine disinfectant compounds. Accordingly, it is counter-intuitive to use sodium bisulfate as a component in the production of chlorine dioxide. Further, in that the reactions described in this invention are far less exothermic than other reactions used to produce chlorine dioxide, the reactions and reaction systems of the current invention are more amenable to in situ and small scale, efficient, and cost-effective production of chlorine dioxide.

Also, although the present invention is described in certain examples below as being used to disinfect the effluent in wastewater treatment plants, it is recognized that the present invention has numerous other applications and is quite versatile. For instance, without being limiting, the reactions, apparatuses, methods and systems of the present invention may be used to disinfect or otherwise treat not only the effluent of wastewater treatment plants, but also the following:

1. the ballast water of ocean-going ships, to kill the larval and adult stages of exotic species that may have been pumped into the bilge at a foreign port, prior to discharging such ballast water at another port (to prevent environmental problems such as the zebra mussel in the United States);
2. disinfecting and/or sterilizing municipal waste, agricultural or other treatment plant process sludges/biosolids;
3. disinfecting sources of water to be used for potable (drinking) water, water used for animal husbandry, or other process waters;
4. washing and disinfecting applications for fruits and vegetables. It is recognized that chlorine dioxide oxidizes certain pesticide residues, making them less harmful to consumers.
5. As a method to provide additional treatment to wastewater in areas of outbreaks of severe acute respiratory syndrome ("SARS"), such as by applying chlorine dioxide so generated to incoming wastestreams to a WWTP, and/or at sites where victims of such syndrome are known to be living.
6. Odor control, to oxidize sulfur compounds, such as hydrogen sulfide, without forming colloidal sulfurs.
7. Generating stocks solutions of chlorine dioxide to treat pulp and paper, to disinfect surfaces, and for other EPA-approved purposes.

The following non-limiting examples are presented to better illustrate the invention.

EXAMPLE 1

Figure 2:
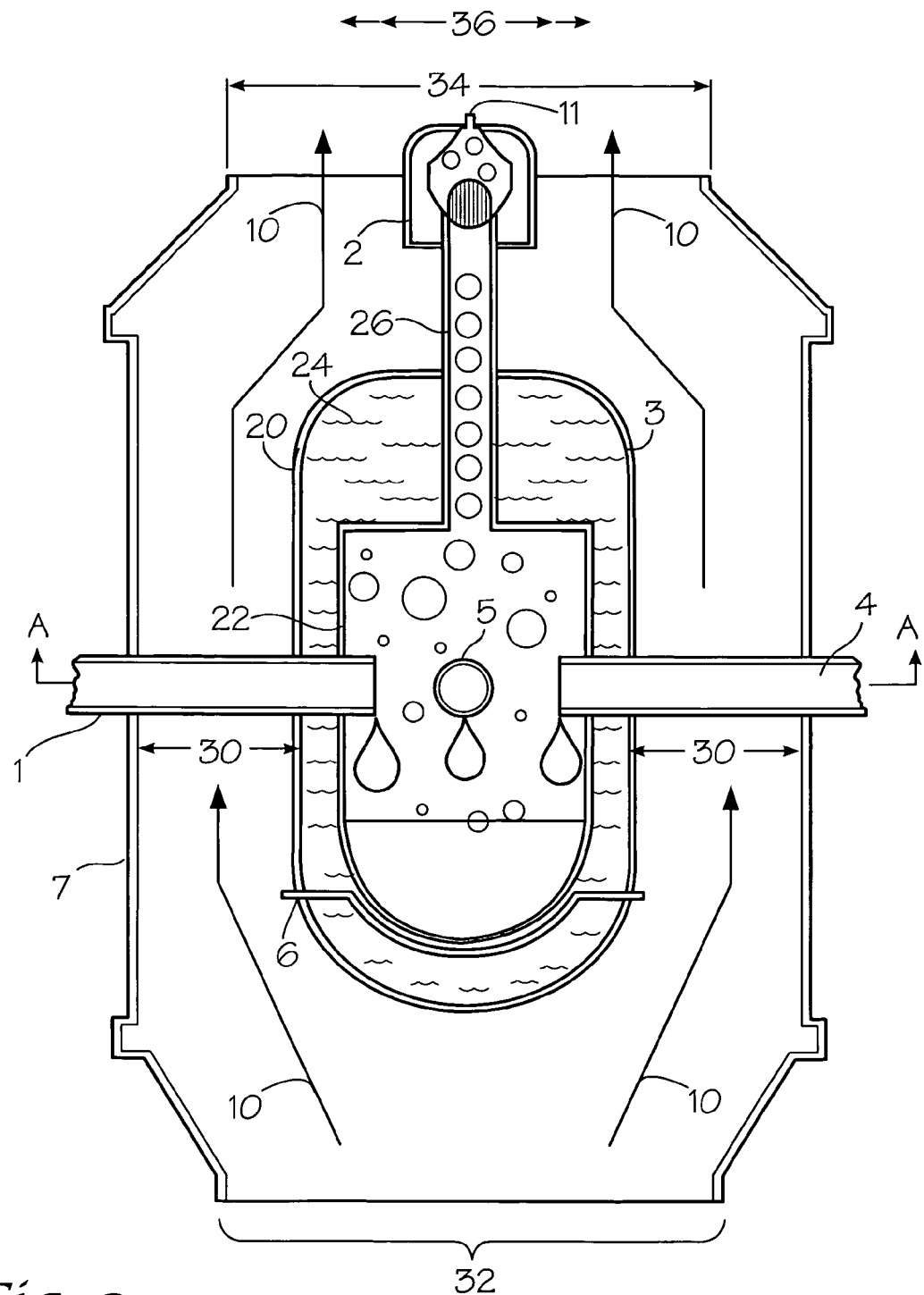
FIG. 2 is a cross-sectional view of one embodiment of the reactor of the present invention, shown within an enlarged area of a water flow pipe into which the chlorine dioxide produced in the reactor is released.
Figure 3:
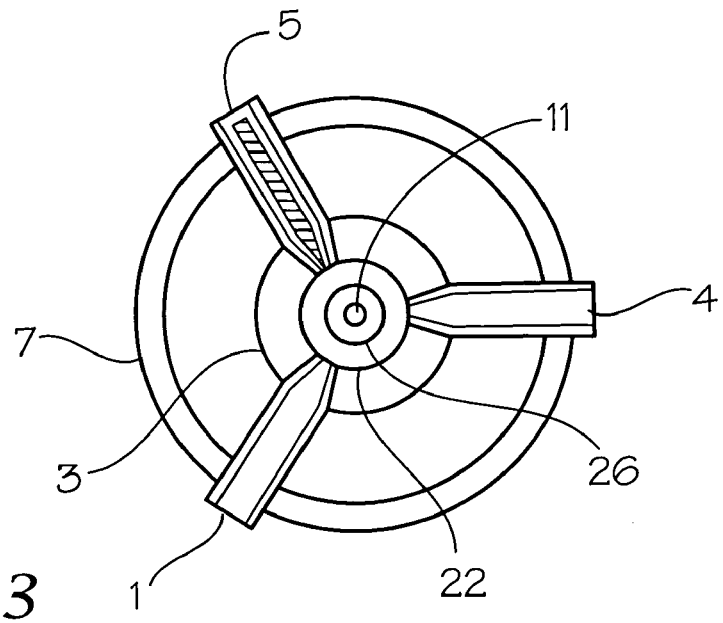
FIG. 3 is a view perpendicular to the view of FIG. 1, taken along the A-A axis in FIG. 1, viewing toward the chamber discharge end, and bisecting each of the three reactant supply pipes.
Figure 4:
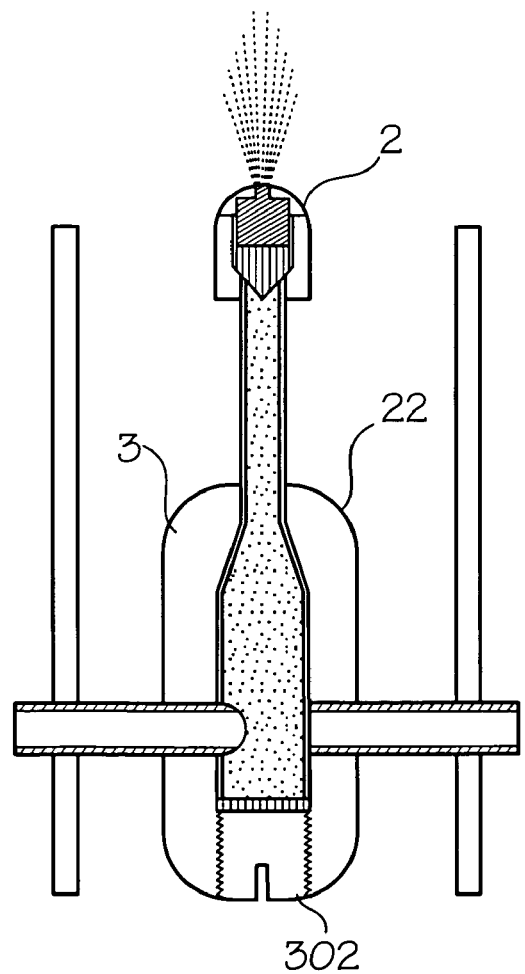
FIG. 4 shows a cross-sectional view of one embodiment of the reactor having an adjustable volume reaction chamber.

One example of the novel reaction chamber is depicted in FIGS. 2-4. The reactor, 20, is comprised of a reactor body, 3, which is preferably cylindrical in cross-section but may be of any three-dimensional shape such that it has sufficient space for the reaction, and sufficient strength to withstand pressures and temperatures to which it is exposed. In the embodiment depicted in FIG. 2, the reactor, 20, also is comprised of a reaction chamber, 22, situated within the reactor body, 3. Insulation, 24, fills the space between the outer walls of the reaction chamber, 22, and the inner walls of the reactor body, 3. It is noted that in other embodiments the reactor body, 3, serves as the reaction chamber itself, and there is no space for intervening insulation.

Where there is a need or desire to better control reaction temperature, a heater, 6, is provided. As shown in FIG. 2, there is no insulation between the heater, 6, and the adjacent bottom surface of the reaction chamber, 22. It is noted that in other embodiments a heater is not present and insulation may occupy all spaces between the reactor body, 3, and the reaction chamber, 22, except where there are structural supports, inlets and outlet pipes, and other structural or control features.

As shown in FIG. 2, three supply pipes, 1, 4, and 5, pass through the reactor body, 3, and open into the reaction chamber, 22. In a preferred embodiment, each of the three pipes, 1, 4, and 5, carry a different reactant into the reaction chamber, 22. In preferred embodiments of the process, these pre-cursor chemicals are delivered under pressure to the reaction chamber, 22, and the reaction chamber, 22, also is under pressure. Optionally, an adjustable pressure actuated check (one-way) valve (not shown in FIG. 2) is present in each of the supply pipes supplying the reaction chamber, 22. These check valves function to keep the reaction contents in the reaction chamber, 22, and to prevent inadvertent back-flow into the supply pipes in case of higher than expected pressure in the reaction chamber, 22, and/or a failure of one or more of the pump or other systems that pressurize the supply pipes.

The reactor, 20, is oriented to have a functional top and bottom. As shown in FIG. 2, the bottom is where the heater, 6, is located. Emanating from the top area of the reaction chamber, 22, is an exit pipe, 26, that passes through the reactor body, 3. Attached at or near the end of the exit pipe, 24, is a discharge check valve, 2. Preferably, this discharge check valve, 2, is adjustable as is the one in FIG. 2. Other orientations as could be designed by one of skill in the art can be envisioned that are within the scope of the present invention. For instance the reactor could be positioned in a generally horizontal fashion and have an exit pipe curved upward with a discharge check valve positioned at the distal end of the pipe. This would represent the functional top (the point at which the product is released under pressure), while the adjacent side closest to the ground or floor would represent the functional bottom.

As depicted in FIG. 2, the reactor, 20, is positioned within an expanded section of pipe carrying water that is to be disinfected by the chlorine dioxide produced in the reaction chamber, 22. In a preferred embodiment, the expanded pipe section, 7, has an approximate diameter that results in a cross-sectional water flow area in section 30 that is about the same as the cross-sectional water flow area of the inflow and outflow pipes, 32 (not shown) and 34, respectively, that are before and after the expanded pipe section, 7, that contains the reactor, 20. In various embodiments, based on the desired type of flow and degree of turbulence in the mixing area 36, where the chlorine dioxide gas begins to mix with the water flow, the respective cross-sectional areas of areas 30, 32, and 34 are set to help effectuate the desired level of laminar flow or non-laminar turbulent flow, and the consequent speed of mixing of the liquid with the chlorine gas. Other methods of controlling laminar flow and/or turbulence, as are known in the art of hydraulic flow mechanics, may also be applied.

FIG. 3 depicts a cross-sectional view of the reactor, 20, and associated structures taken along lines A-A of FIG. 2. Shown in FIG. 3 are the cross-sections of the expanded pipe section, 7, the reactor body, 3, the reaction chamber, 22, the exit pipe, 26, and the discharge orifice, 11. Laterally bisected in this view are three supply pipes, 1, 4, and 5.

The reactor, 20, described above operates in one embodiment of the methods of this invention as follows. Three pre-cursor chemicals, one from each of the three supply pipes, 1, 4, and 5, are pumped into the reaction chamber, 22, under pressure. The three pre-cursor chemicals are sodium hypochlorite (a halogen donor), sodium chlorite (a chlorite donor), and sodium bisulfate. The sodium bisulfate is acidic and its relative level of addition is adjusted to help control the rate of the reaction to chlorine dioxide. Further, while not being bound to a particular theory, laboratory experiments and field trials appear to indicate that the addition of sodium bisulfate reduce the levels of undesirable residuals in the product mixture.

These pre-cursor chemicals, even when supplied as technical or commercial grades, react in the reaction chamber, 22, under desired pressure and temperature conditions, to produce chlorine dioxide with low to no unwanted disinfection byproducts.

Such unwanted disinfection byproducts include total trihalomethanes (TTHMS) and haloacetic acids (HAAS). In one or more embodiments, the relative concentrations of the three pre-cursor chemicals are sodium chlorite, sodium bisulfate, and sodium hypochlorite, are adjusted to permit a desired outcome as far as the concentration and yield of chlorine dioxide, and the nature of the reaction byproducts. In other embodiments, urea sulfate, or any organic acid blend, can be substituted for sodium bisulfate. Similarly, in place of sodium hypochlorite, hypochlorous acid may be substituted.

The pumps used to pump the pre-cursor chemicals through pipes, 1, 4, and 5 are positive displacement pumps, or other pumps capable of delivering the pre-cursor materials (typically solutions) under pressure against a back pressure in the reaction chamber, 22. This serves to build pressure to a desired level. The discharge check valve, 2, sets the high end of pressure in the reaction chamber, 22, in that once pressure builds as a result of the pumps delivering the pre-cursor materials, and as a result of the reactions taking place in the reaction chamber, 22, the discharge check valve, 2, opens at its set pressure point, releasing chlorine dioxide (and, typically, water in the form of steam or spray liquid, which was the solvent for the pre-cursor chemicals supplied through pipes, 1, 4, and 5).

In operation, the reaction chamber can be operated by setting the rates of the pumps delivering the pre-cursor materials (reactants), by monitoring the level of chlorine dioxide that is discharged, and by periodically adjusting the pump rates for each of the pre-cursor materials (reactants) until a desired, acceptable or targeted production rate and/or efficiency is obtained. Alternately, a microprocessor, a special-purpose computer, or a general-purpose computer appropriately programmed for the purpose, may be operatively linked to the pumps, and to one or more detectors or sensors of chlorine dioxide (or other parameter, including but not limited to total oxygen demand, chemical oxygen demand, total organic carbon, or biological oxygen demand) downstream of the discharge of chlorine dioxide into the flow of liquid into which it was discharged from the reaction chamber. So linked and programmed, this can automatically monitor the desired endpoint parameter and adjust the rates of inputs of the reactants to reach and/or maintain a desired, acceptable or targeted production rate and/or efficiency.

In one or more embodiments, a delivery tube is added for the addition of solids as needed. Also, in one or more embodiments, there is no need to drain off water, since it gets expelled under pressure either as steam or liquid water, the latter typically in the form of spray or droplets.

In one or more embodiments, the range of operating temperature is about 40 to about 185 degrees Fahrenheit. A narrower but acceptable operating range is about 75 to about 145 degrees Fahrenheit, and an even narrower but acceptable operating range is about 75 to about 120 degrees Fahrenheit. The operating temperature range for a particular application of the reactor of the present invention will depend upon a number of factors, including but not limited to the quality and grade of the pre-cursor chemicals, the types and levels of particular contaminants, the desired output (balancing yield with production of certain byproducts, etc.), the system into which the product is being dispersed, and the regulations in place regarding levels of residuals and contaminants.

In one or more embodiments, the range of operating pressure is about 25 to about 200 pounds per square inch (psi). A narrower but acceptable operating range about 30 to about 90 psi, and an even narrower but acceptable operating range is about 40 to about 75 psi. The operating pressure range for a particular application of the reactor of the present invention will depend upon a number of factors, including but not limited to the quality and grade of the pre-cursor chemicals, the types and levels of particular contaminants, the desired output (balancing yield with production of certain byproducts, etc.), the system into which the product is being dispersed, and the regulations in place regarding levels of residuals and contaminants.

The above-described system provides consistent output of chlorine dioxide over extended periods of operation. Further, the level of chlorine dioxide output can be regulated by modulation of the amount of sodium hypochlorite (a halogen donor), by adjusting the strength of this solution entering the chamber, the delivery rate by the pump inputting this pre-cursor material, or by any other mechanism of modulation known to those of ordinary skill in the art.

Another approach to control output is to adjust the volume of the reaction chamber itself. One way to do this is shown in FIG. 4, in which a bottom section, 302, of the reaction chamber, 22, is rotatably screwable into the body of the reactor body, 3. As appropriate for a specific application, such as for certain embodiments in which it is desired to adjust the chamber volume to correlate with the relative production levels of chlorine dioxide required, the volume of the reaction chamber, 22, is adjusted initially by screwing the bottom section, 302, inward or outward to decrease or increase the volume of the reaction chamber, 22. Further adjustment may be made as needed after the performance of the unit is assessed. This type of adjustment, which is not limited to the disclosed screw-bottom mechanism, permits a single chamber to function to produce chlorine dioxide across a wider range of outputs.

Through experimentation with the reaction chamber, it also has been learned that chlorine dioxide can be produced through the reaction of only two reactants, namely sodium chlorite and sodium bisulfate. For instance, using stock nominal concentrations of 20 percent or 31.25 percent sodium chlorite in combination with 22 percent sodium bisulfate, chlorine dioxide was produced in the reaction chamber. Thus, a halogen donor is not an absolute requirement when these reactants are used at or around these concentrations. Therefore, it is believed that over a range of concentrations and conditions, such as can be determined without undue experimentation by one of ordinary skill in the art, a wide range of respective concentrations for sodium chlorite and sodium bisulfate can be determined at which acceptable yields of chlorine dioxide are obtained, without the need to add a halogen donor. Also, while not being bound to a particular theory, a halogen donor such as sodium hypochlorite or hypochlorous acid may be used initially, and then its addition suspended once the reaction is established and a sufficient quantity of halogen donors (formed as products) exist in the reaction chamber. Also, while not being bound to a particular theory, substitution of urea sulfate, or any organic acid blend, for sodium bisulfate, may also yield chlorine dioxide when combined with sodium chlorite.

Further, in one or more embodiments of the present invention, as depicted in this, in other examples, or in any apparatus of the present invention as defined by the claims appended hereto, the reactor and the system can be modified to provide suitable species of residual chlorine. For instance, in water purification and distribution systems where a residual chlorine species is desired, for instance in a potable water distribution system, chloramine species may be desirable to provide more persistent secondary disinfection well beyond the chlorine reactor, 20. In such situations, one variation of the above method is to add a proportionate amount of ammonia. This typically is done with a separate supply pipe, entering the water stream downstream of the reaction chamber, 22, going directly into the flow of liquids after the chlorine dioxide has been added from the 1 reaction chamber (not shown in FIG. 1). The location of the supply pipe for such addition of ammonia (or other chemical addition to provide a more persistent secondary disinfection in the flow typically is placed at a downstream point at which the chlorine dioxide has become well dispersed into the flow. While not being bound to a particular theory, it is believed that the ammonia binds with excess free chlorine and thereby forms chloramines. These chloramines are preferable to more toxic undesired byproducts, such as TTHMS and HAAS, and as noted perform as a residual chlorine species to provide secondary disinfection in the distribution pipes.

The embodiments depicted in FIGS. 1-3 placed the reactor within a larger pipe carrying the flow of liquid which was the major flow to be treated with the product of the reactor. This adds a safety factor in that the product is produced very close to where it is substantially diluted to the final concentration for disinfection, bleaching, etc. However, the reactor alternatively can be placed apart from the major flow pipe or channel into which the product is to be distributed.

For instance, the reactor can be outside of any pipe carrying a liquid into which the product is released. In this configuration, the point of release of the product, for instance chorine dioxide as described in the reactions above, can be situated within a flow of liquid. This is done, for example, by positioning the reactor close to the pipe or channel carrying the flow of liquid, and positioning a pipe bearing the reactor discharge pipe in that flow of liquid. Further, that flow of liquid may be the major flow pipe or channel (i.e., the ultimate destination, in which the final diluted concentration is achieved), or that flow of liquid may be an intermediate stream which is thereafter distributed to a larger flow as a "stock solution" or "concentrate" of the product. In the latter case, the intermediate stream is then distributed to one or more entry points of the larger flow (e.g., the ultimate destination).

Further, regarding introduction of product into a "stock solution" intermediate flow stream, this can be done as described above, from a reactor not positioned within the pipe carrying this flow stream, or, alternatively, the reactor can be placed within the pipe or other vessel carrying the intermediate flow stream. Once the product is so introduced into the intermediate flow stream, the intermediate flow stream is directed to one or more sites of release into a larger flow stream, at which point the product becomes accordingly diluted.

EXAMPLE 2

This section provides a range of different design examples, or embodiments, of the reactor chamber, with a variety of basic and optional features. This is provided to indicate, without being limited by these examples, the scope of the claimed invention with regard to the types and variations and optional features of a reaction chamber of the present invention (and the reactions that may take place therein).

Many of these embodiments shown in the figures of this example are shown without specific structural supports that position and structurally support the reactor, 20, within the water stream, 10, of the larger supply pipe, 7. However, this is done to keep the figures below relatively simple in presentation. It is axiomatic that support structures are present in all such figures where they are not specifically shown.

Also, for convenience in presenting figures similar to FIGS. 1-3, the reactors, 20, are shown in expanded regions of pipe, i.e., the expanded pipe section, 7. However, it is appreciated that, especially for relatively large pipe diameters, where the cross-sectional area of the reactor, 20, is relatively small in comparison to the cross-sectional area of the water pipe into which it is placed, the water pipe need not be expanded at the section where the reactor, 20, is placed. For instance, without being limiting, a relatively large pipe diameter, where the reactor's cross-sectional area is less than twenty percent of the water pipe's cross-sectional diameter, the water pipe preferably is not expanded at the section where the reactor, 20, is placed. This will result in a net friction loss, but will provide increased turbulence that will facilitate rapid mixing of the chlorine dioxide with the water in the pipe upon release of the chlorine dioxide from the discharge orifice of the reactor. Standard hydraulics and engineering will dictate whether an expanded section of the water pipe is needed for placement of the reactor within the pipe.

Referring to FIG. 4, FIG. 4 is a cross-sectional view of an embodiment of the reactor of the present invention, shown within an enlarged area of a water flow pipe into which the chlorine dioxide produced in the reactor is released. In this embodiment the reactant supply lines, 1, 4 and 5, enter the reactor chamber from one end, and the discharge check valve, 2 (releasing chlorine dioxide), is at the opposite end of the reaction chamber. In this figure, the exit pipe, 26, is centrally located at one end of the reaction chamber, 22. However, it is appreciated that in other embodiments, such as when the reaction chamber, 22, is oriented in a horizontal plane from one end to the other, the exit pipe, 26, may be positioned toward the gravitational top of the end of the reaction chamber, 22, so as to facilitate the release of the chlorine dioxide gas, and to lessen accumulation of such gas in a void that cannot be readily discharged via the discharge check valve, 2.

Figure 5:
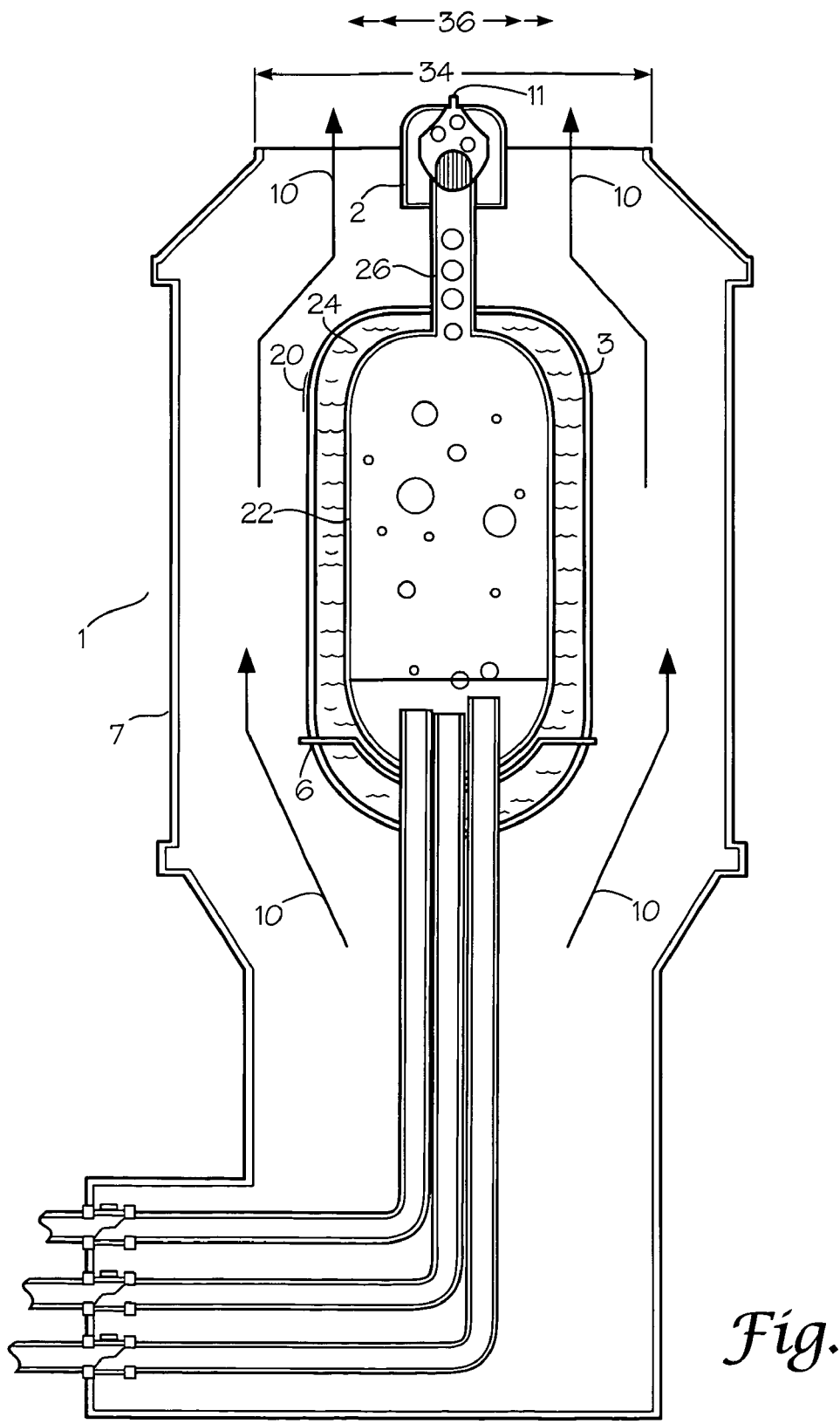
FIG. 5 is a cross-sectional view of an embodiment of the reactor of the present invention, shown within an enlarged area of a water flow pipe into which the chlorine dioxide produced in the reactor is released. In this embodiment the reactant supply lines enter the reactor chamber from one end, and the release nozzle (releasing chlorine dioxide) is at the opposite end of the reaction chamber.

FIG. 5 is a cross-sectional view of an embodiment of the reactor of the present invention, shown within an enlarged area of a water flow pipe into which the chlorine dioxide produced in the reactor is released. In this embodiment the reactant supply lines enter the reactor chamber from one end, and the release nozzle (releasing chlorine dioxide) is at the opposite end of the reaction chamber. Two reactant lines (i.e., supply lines), 4 and 5, empty into the reaction chamber closer to the far left end of the reaction chamber, 22, allowing a longer and earlier reaction association of the chemicals from these reactant supply lines, 4 and 5. The third line supply line, 1, empties into the reaction chamber at a position farther into the reaction chamber.

Figure 6:
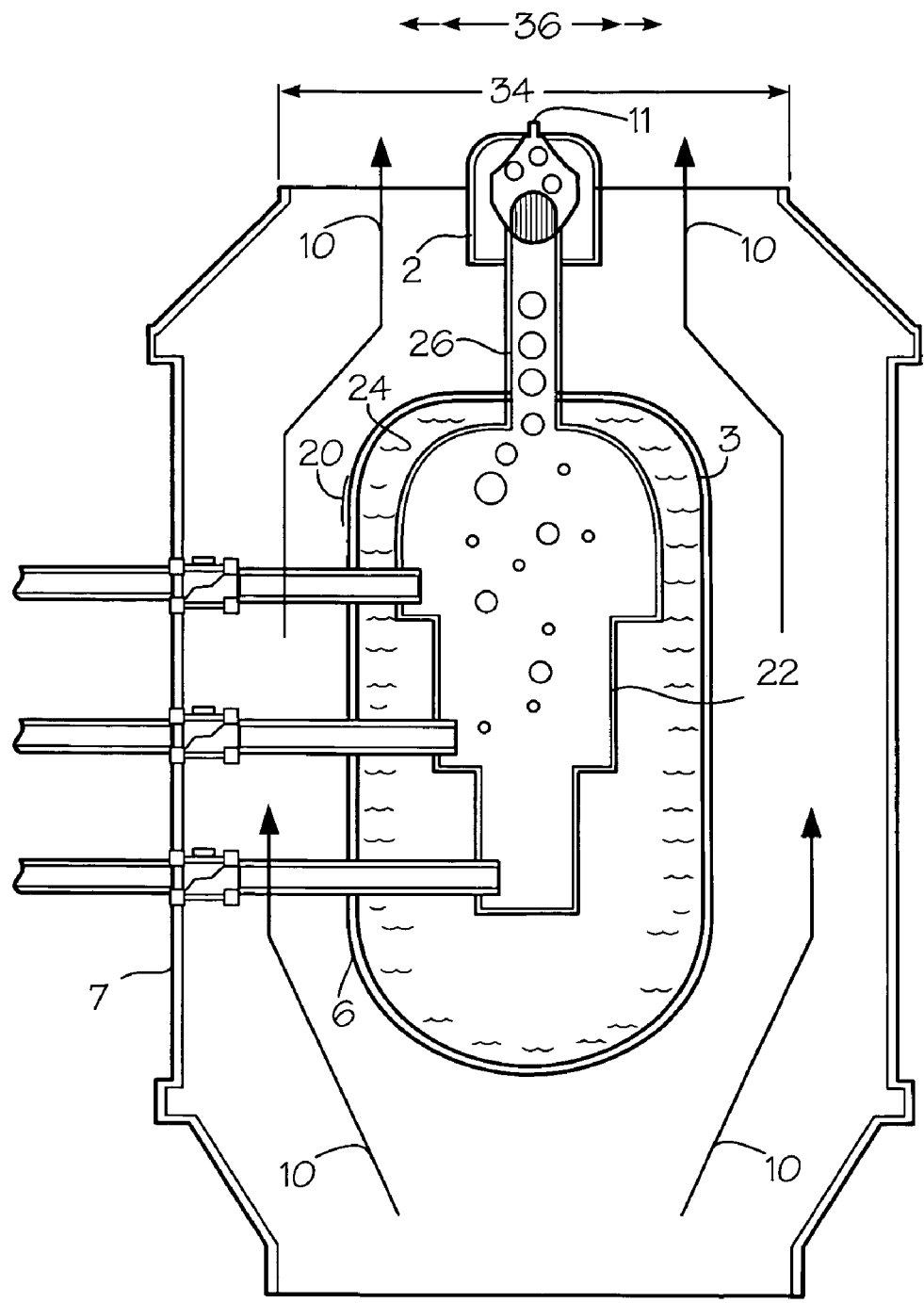
FIG. 6 is a cross-sectional view of an embodiment of the reactor of the present invention, shown within an enlarged area of a water flow pipe into which the chlorine dioxide produced in the reactor is released. In this embodiment the reactant supply lines enter the reactor chamber from one end, and the release nozzle (releasing chlorine dioxide) is at the opposite end of the reaction chamber. The reactant lines empty into the reaction chamber at different distances from the nozzle, allowing a stepped reaction association of the chemicals from these feed lines.

Such orientation of the feed lines is appropriate where it is desired to have two reactants, such as a the chloride source, like sodium chlorite from supply pipe 4, and an acid source like sodium bisulfate from supply line 5, initially react for a period prior to exposure to the chlorite donor, such as sodium chlorite, which enters more centrally in the reaction chamber, 22, through supply pipe 1. This sequencing of reactants also is shown in FIG. 6.

Figure 7:
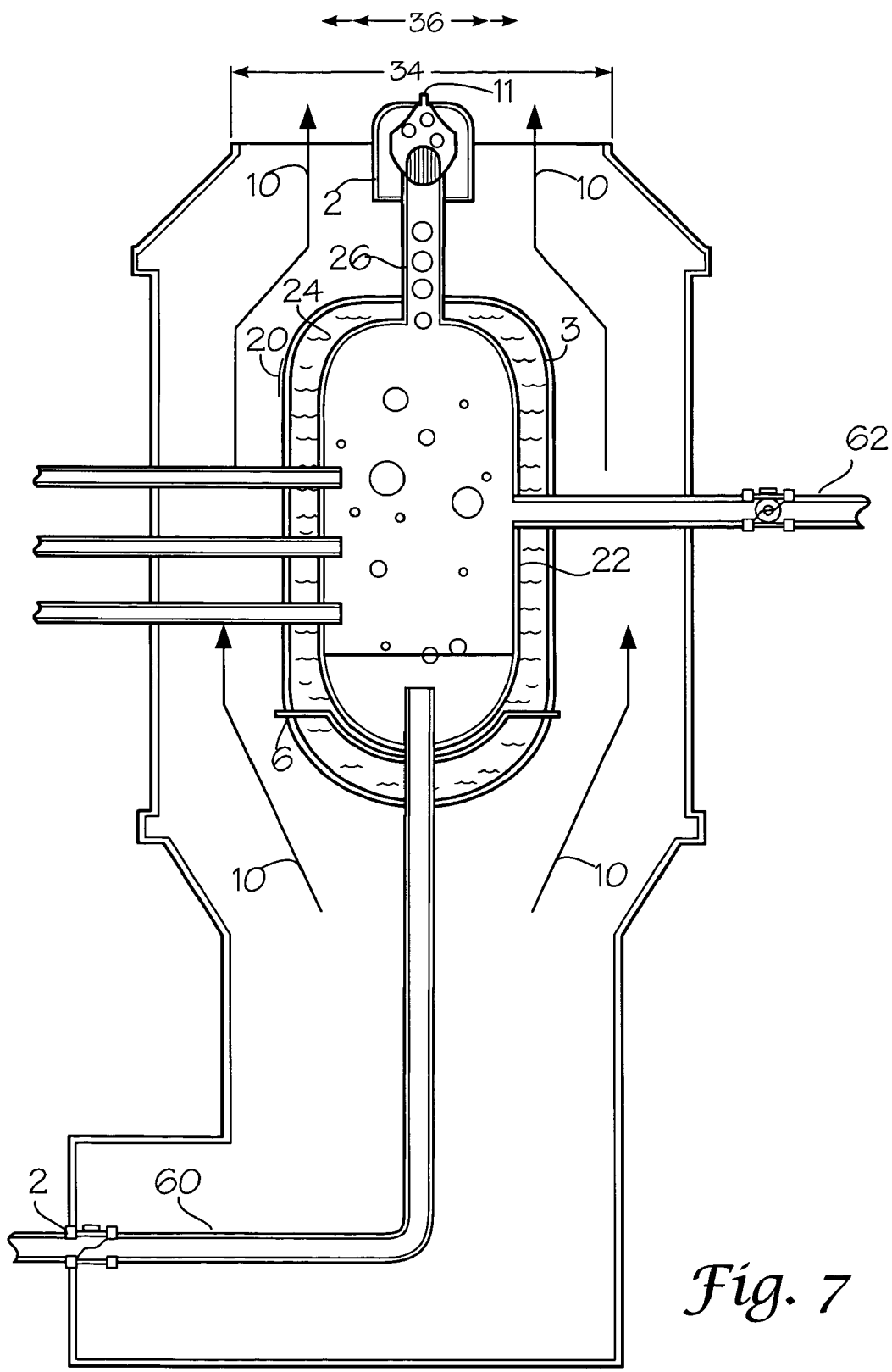
FIG. 7 depicts an embodiment of a reaction chamber of the present invention, which additionally comprises a bottom-positioned drain line that is suited to drain settled material from the reaction chamber and a rear positioned flushing line to be used either during operation or during clean-up of the chamber at shut-down.

FIG. 7 has both a top-positioned fourth supply pipe, 60, and a bottom-positioned drain line, 62 that is suited to drain settled material from the reaction chamber. The drain pipe, 62, may operate either during operation or during clean-up of the chamber at shut-down. For instance, it may be used in conjunction with the periodic addition during operation of a strong acid via the top-positioned fourth supply pipe, 60. This periodic addition serves to dissolve and remove build-up of mineral deposits (such as when a calcium bisulfate or a calcium chlorite is used) that may be occurring within the reaction chamber, 22.

It is noted that the top-positioned fourth supply pipe, 60, and the bottom-positioned drain line, 62, may be added independently or together to any configuration of reaction chamber in which their respective functions are needed.

Figure 8:
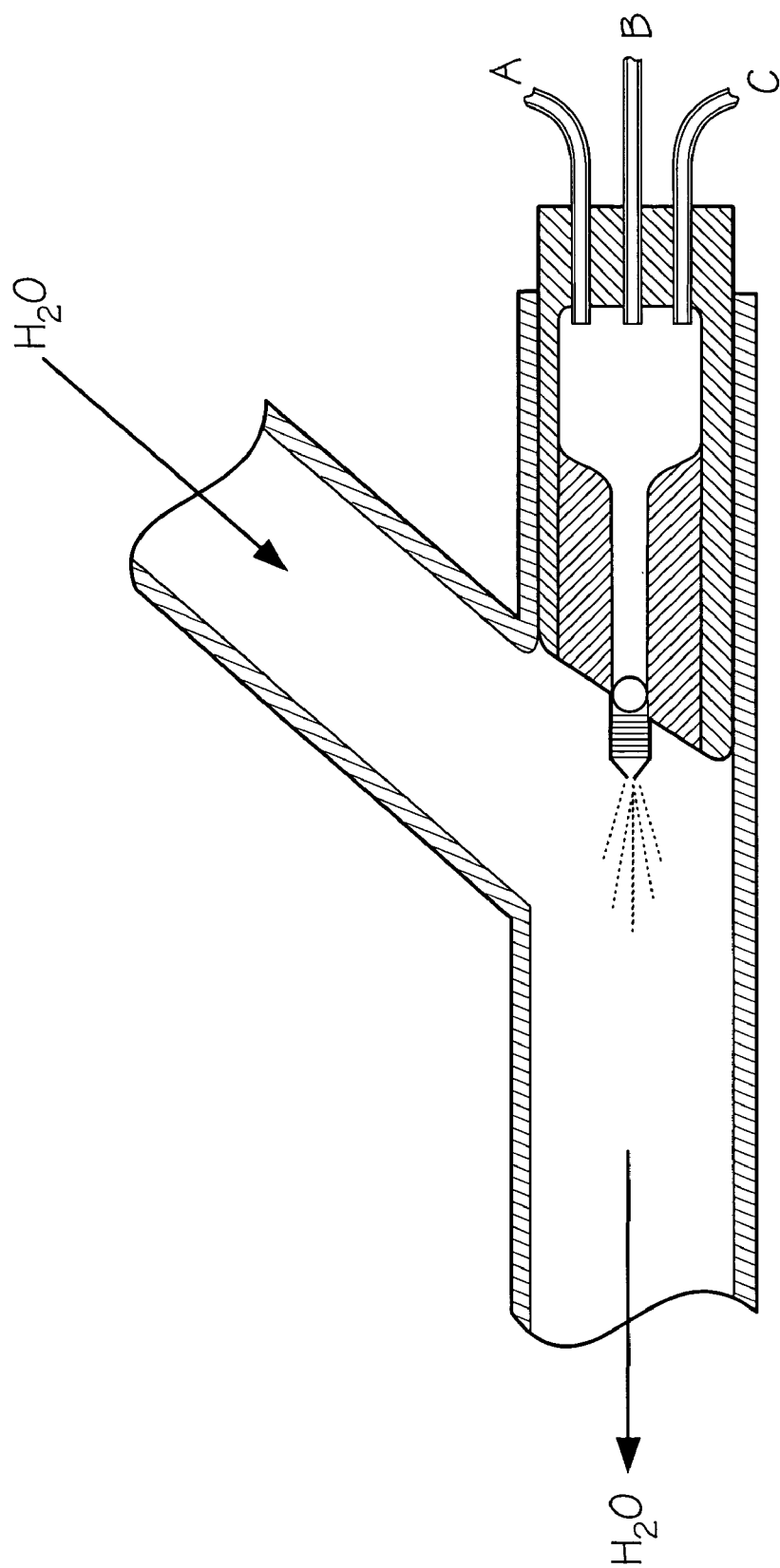
FIG. 8 is a cross-sectional view of an embodiment of the reactor of the present invention, shown within an enlarged area of a water flow pipe into which the chlorine dioxide produced in the reactor is released. In this embodiment the reaction chamber is positioned into one of three legs of a PVC "Y" coupling. In this particular embodiment, the reaction chamber is constructed of one piece of plastic material (such as CPVC or PTFE) that has been machined to provide the hollow cavity as a reaction chamber and three bored chemical feed entrances to this cavity. Also, spaces for check valves are provided in this single piece, and check valves are placed therein. Water inflow and outflow are through the other two legs of the "Y" coupling.

FIG. 8 is a cross-sectional view of an embodiment of the reactor of the present invention, shown within an enlarged area of a water flow pipe into which the chlorine dioxide produced in the reactor is released. In this embodiment the reaction chamber is positioned into one of three legs of a PVC "Y" coupling. In this particular embodiment, the reaction chamber is constructed of one piece of plastic material (such as CPVC or PTFE) that has been machined to provide the hollow cavity as a reaction chamber and three bored chemical feed entrances to this cavity. Also, spaces for check valves are provided in this single piece, and check valves are placed therein. Water inflow and outflow are through the other two legs of the "Y" coupling. The actual connection of this Y coupling reactor to the existing piping of the rest of the system is done by any of the standard connection means, including but not limited to: thread; slip; o-ring.

Figure 9B:
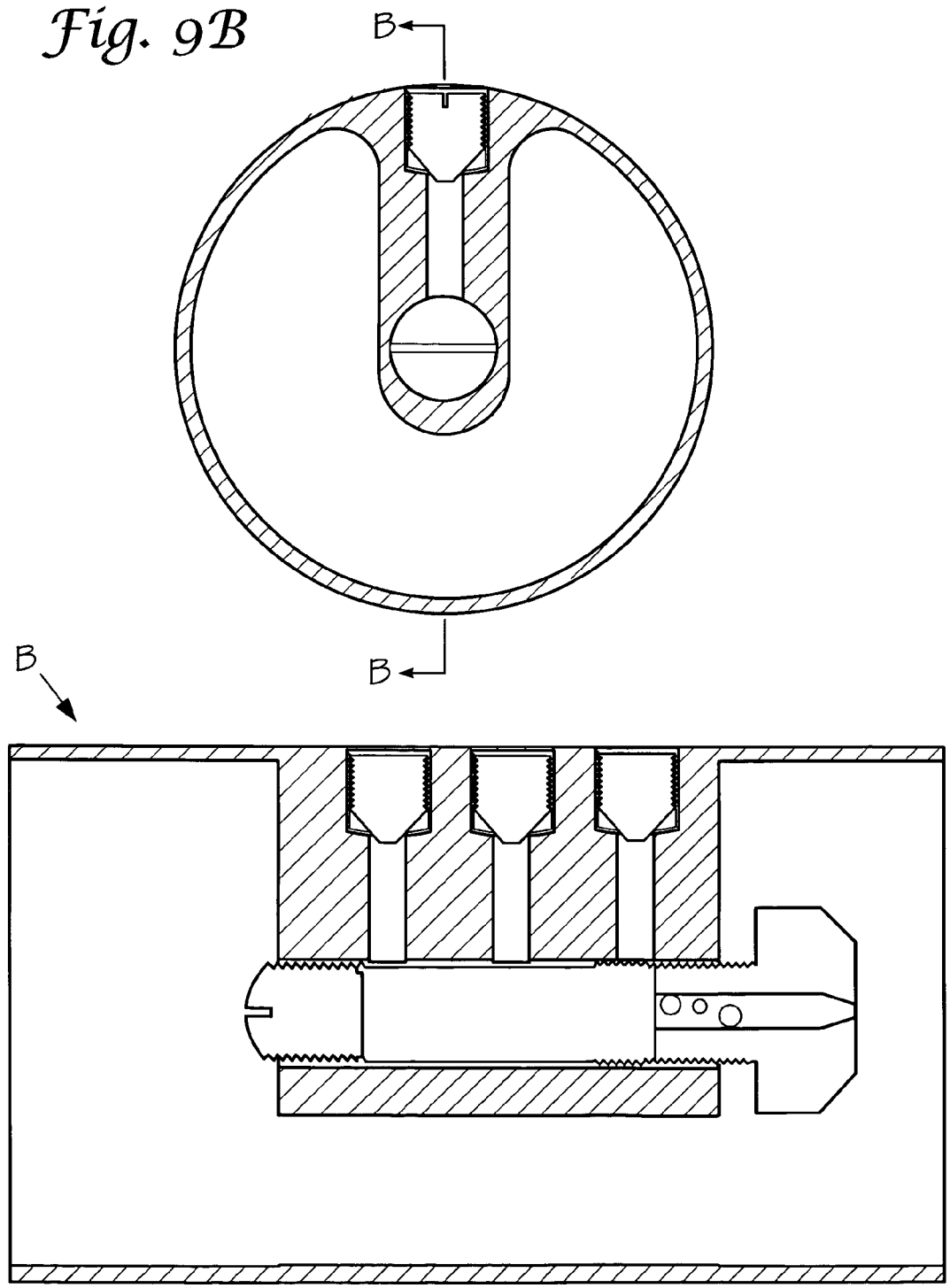
FIG. 9B depicts a reactor also machined from a CPVC or other appropriately chemically resistant plastic block, however machined to provide a single large channel through which water flows, cooling the reaction chamber. The chemical injection points are through three bored chemical feed entrances positioned in line relative to each other. The chemicals enter in a sequential arrangement in relation to either end of the reaction chamber. Also, spaces for check valves are provided in this single piece, and check valves are placed therein.

FIG. 9A is a cross-sectional view of an embodiment of the reactor of the present invention. This reactor embodiment is machined from a CPVC or other appropriately chemically resistant plastic block, providing three channels through which water flows, cooling the reaction chamber. The chemical injection points are through three bored chemical feed entrances positioned at 120 degrees relative to each other. The chemicals directly impinge and mix at a central point. Also, spaces for check valves are provided in this single piece, and check valves are placed therein. FIG. 9B depicts a reactor also machined from a CPVC or other appropriately chemically resistant plastic block, however machined to provide a single large channel through which water flows, cooling the reaction chamber. The chemical injection points are through three bored chemical feed entrances positioned in line relative to each other. The chemicals enter in a sequential arrangement in relation to either end of the reaction chamber. Also, spaces for check valves are provided in this single piece, and check valves are placed therein.

FIG. 10 is a diagrammatic view of an embodiment of the present invention which uses a positive-displacement pump to draw the reactants into a reaction chamber of the present invention. The reactants mix, react, and the end-products, largely chlorine dioxide gas, are pumped out by the same pump.

FIG. 11 is a diagrammatic view of an embodiment of the present invention which utilizes commercially available CPVC pipe fittings to form a reactor of the present invention. In this embodiment, a standpipe is at the gravitational bottom of the reactor so constructed, providing for a pooling or mixing effect at the bottom of the reaction chamber. As chemical reactant liquids are pumped into the chamber, they accumulate or pool at the bottom, react, form chlorine dioxide which is in gas and solution form. Gas and liquid from this chamber are expelled through the opening of the standpipe, and go therefrom into the stream of the water to be disinfected.

Figure 12:
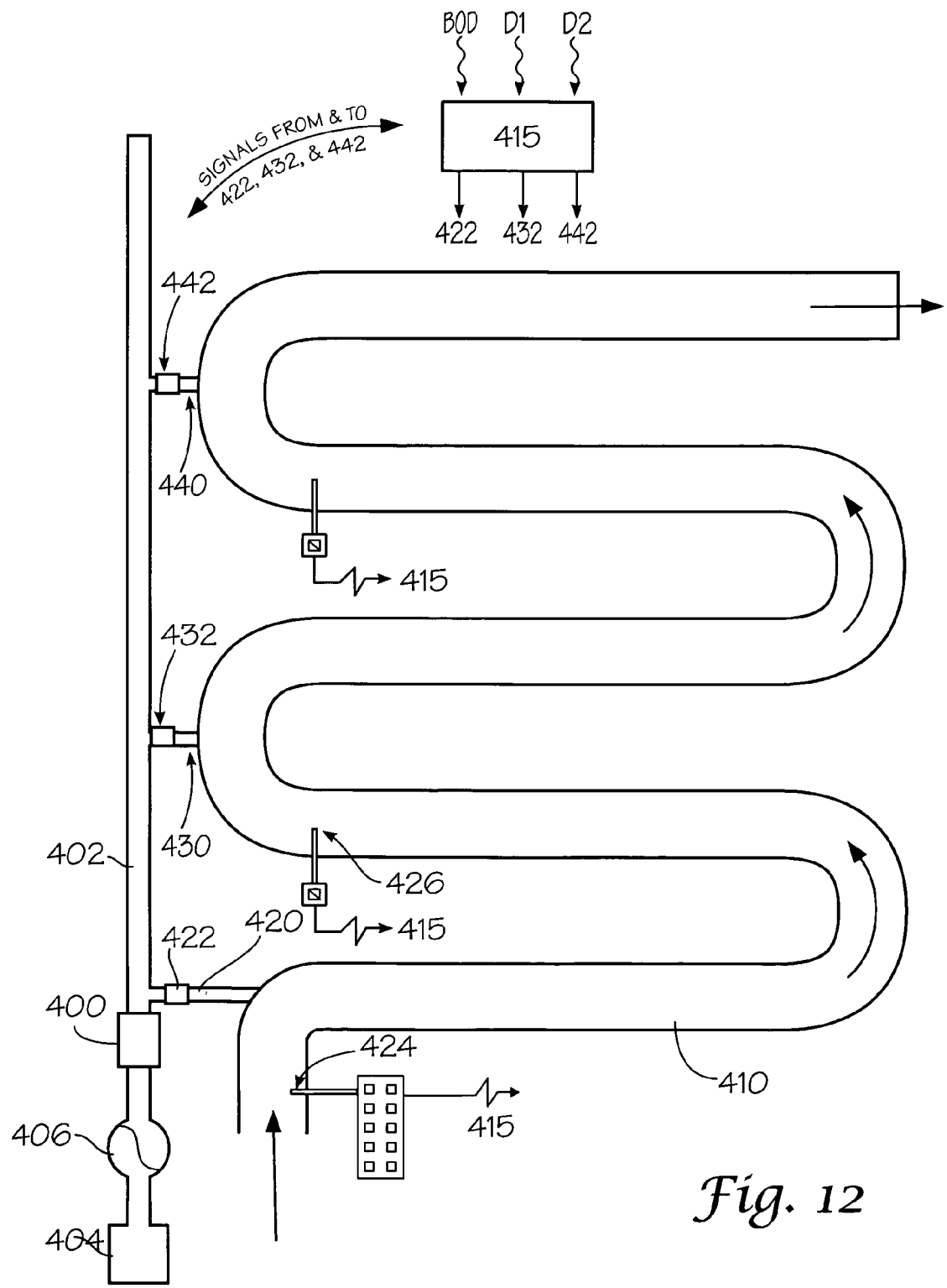
FIG. 12 diagrams a large water flow being disinfected at more than one point by inputs of chlorine dioxide, where the amounts added at the inputs are controlled by a centralized processing system that receives data from more than one point along the large water flow.

FIG. 12 diagrams a large water flow being disinfected at more than one point by inputs of chlorine dioxide, where the amounts added at the inputs are controlled by a centralized processing system that receives data from more than one point along the large water flow.

For any of the above embodiments, or for other configurations of the present invention, the flow of water passing the in situ reactor may be from either direction, that is, from the non-nozzled end or from the nozzled end.

Further, it is appreciated that those of ordinary skill in the art, with ordinary knowledge of mechanical and hydraulic engineering, may, upon studying the disclosure and examples of this invention, develop reactor chamber designs and operational modes that are not exactly what is shown herein. Such modified designs, developed from the disclosed invention, are nonetheless within the scope of the present invention when practicing one or more of the appended claims.

EXAMPLE 3

Another aspect of the present invention is a demand-based automated dosing system of adding chlorine dioxide to a waste stream or other flow of liquids requiring the addition of chlorine dioxide or other species of compounds made by the chamber of the present invention. This automated process for monitoring and delivering chlorine dioxide to more than one point is shown in FIG. 12. A reactor, 400, is positioned along a pipe, 402, that originates from a source (i.e., a well or municipal supply system). Optionally, a pump, 406, pressurized the system if the pressure is not sufficient from the source, 404. Chemical inputs (not shown) supply the reactants to the reactor, 400, and the product, chlorine dioxide, is added to the pipe, 402, at or near the site of the reactor, 400 (depending on which of the above described configurations are used to position the reactor in relation to the pipe). A major flow channel, 410, in need of receiving the product, in this example being chlorine dioxide, receives a primary dosage of product through pipe 420. The flow of intermediate concentration liquid from pipe 402 through pipe 420 into point A of the flow in major flow channel 410 is controlled by a controller, 422. The controller may be a metering pump, a solenoid controlled valve, a metering valve, or any other means of regulating fluid flow such as known to those of ordinary skill in the art. In one or more embodiments, a microprocessor, a special-purpose computer, or a general-purpose computer appropriately programmed for the purpose, represented in FIG. 4 as 415, sends signals to the controller, 422. These signals optionally are based in part on the parameters (including but not limited to total oxygen demand, chemical oxygen demand, or biological oxygen demand) as estimated or determined by an operator attending to the system, or by single or ongoing chemical analysis taken at sampling point 424. The chlorine dioxide is consumed as the flow moves to sampling point 426. At that point samples as taken, filtered as needed through an appropriate filter, for instance a 10-micron particle filter, and analyzed in detector D1 for residual levels of chlorine (in the form of chlorine dioxide). Signals of such results are transmitted to 415. After appropriate computation, a signal is sent, as needed, to boost the level of chlorine dioxide in the flow in 410 by adding additional concentrate from pipe 402 through pipe 430, which is controlled by controller 432. The controller receives signals from 415, which regulates how much, if any, concentrate is added through pipe 430.

The system of FIG. 12 and similar systems are believed to provide an improved approach to dealing with varying demands and loads in typical wastewater and other treatment systems. By determining the reduction of oxidant at one or more points after the initial addition, subsequent additions can be more appropriately made. This can decrease overall usage of oxidants as well as more finely tune their additions, further resulting in less active and residual products being released to a natural body of water.

It is noted that for this and other embodiments, the signals from the detectors or from other sensors may be communicated by any way known to those of skill in the art. The signals can be communicated by conventional means, such as by sending electrical impulses along a conducting wire, fiber optics, by more sophisticated means, such as by converting the signals into radio waves and transmitting these waves such that a receiver receives the signals and thereafter sends them to the microprocessor (i.e., any means of telemetry), special-purpose computer, or general purpose computer represented in FIG. 12 as 415, or by any other way now known or later developed. Similarly, signals between 415 and each controller may likewise be communicated by any way now or later developed.

EXAMPLE 4

Also, the present system and methods include a step of destroying excess chlorine dioxide or other oxidants present in a flow of liquid by exposing such flow to ultraviolet light of sufficient intensity. A need may exist in a particular application of the present reactor, system and methods of production of chlorine dioxide, to reduce the level of chlorine dioxide after a certain point in the system. For instance, after sufficient residence time of exposure to chlorine dioxide, a liquid may be effectively disinfected. Excessive reactive chlorine dioxide in the liquid stream after that point may lead to excessive corrosion, toxicity to users, or other undesired consequences. A preferred way to reduce the concentration of chlorine dioxide in this case is to outfit a vessel or tank or chamber with a single or an array of ultraviolet lamp(s) mounted to expose the flow of the liquid to ultraviolet radiation at sufficient levels, based on the flow rate and depth of the flow past the lamp or lamps, to remove the necessary quantity of excess chlorine dioxide. It is widely known that ultraviolet radiation does not effectively penetrate water beyond a certain depth, depending on the intensity of the radiation and other factors. Accordingly, the flow and depth are adjusted to provide the necessary exposure time to the ultraviolet radiation to be effective. A patent, U.S. Pat. No. 6,171,558, deals with the use of ultraviolet radiation for another application. For the background provided in that patent, it is incorporated by reference into this disclosure. Further, based on the information in U.S. Pat. No. 6,171,558, the frequency of ultraviolet radiation to break up chlorine dioxide into chlorites and chlorates, to control high levels of chlorine dioxide, is likely above 30 nannohertz.

EXAMPLE 5

A two-phase on-site study investigated embodiments of the presently described invention system and apparatus for generating aqueous chlorine dioxide ($ClO_2$) for the disinfection of municipal wastewater. The first phase, described in this example, was directed to preliminary testing to target dosage levels that would provide sufficient disinfection whilst obtaining acceptable end-of-pipe, effluent toxicity based on bioassays using representative marine/estuarine test organisms. The first phase also included the testing of a small-scale replica of the plant operation (post clarifier).

The second phase, described in the next example, used embodiments of the system and apparatus of the present invention to disinfect the actual wastestream of a municipal wastewater treatment plant ("WWTP"). This study took place on site at two WWTPs in Florida.

At the first WWTP, $ClO_2$ was injected into post clarifier effluents in a laboratory environment to determine the dosing requirements needed for effective bacterial control. After the desired disinfectant levels were achieved, marine organisms were subjected to these treated effluents to observe their survivability.

Next, at the same WWTP, using the information gathered from the laboratory testing, a small-scale replica of the plant operation (post clarifier) was constructed as a side stream project. This small-scale pilot successfully operated under a wide range of actual operational variables that occurred in the plant during numerous test periods. Desired disinfectant levels were maintained during these tests without impacting the plant's final discharge water quality.

The initial study began with the sampling of post clarifier effluent to determine the bacterial count prior to standard chlorination at the WWTP. Numerous samples were taken over several weeks and diluted with de-ionized (DI) water at a 100 to 1 ratio. These samples were then cultured, incubated and analyzed for their bacterial concentrations. It was determined that the bacterial count was ranging from 12,000/100 ml to 24,400/ml. of effluent, or an average of approximately 18,000/100 ml of effluent.

With this information, samples of the post clarifier effluent were dosed with $ClO_2$ in the laboratory to determine the most effective dosage rate to effectively control bacteria. The dosing ranged from 0.3 ppm to 3.0 ppm. Samples were again taken over a 7-day period to assure repeatability and to accurately determine the $ClO_2$ dosing rate for the eventual side stream pilot. In addition to the bacterial counts, some of the samples were tested for their overall toxicity. Test species were the mysid shrimp, *Mysidopsis bahia*, and the inland silverside minnow, *Menidia beryllina*.

With this accumulated data, the plant's operation (post clarifier) was replicated in scale. The source water for the side stream pilot was water coming from the clarifier. This water was then to be dosed to evaluate the effectiveness of the $ClO_2$ generator and its ability to replicate the dosing rates established earlier in the laboratory samplings. The pilot consisted of the following equipment: (1) a raw water pump, (2) the $ClO_2$ generator, (3) a mixing chamber, (4) a contact chamber with 2 and 5 minute sampling points, (5) contact reservoir to allow an additional 30 minutes of contact time, and (6) an aeration basin.

For both WWTP 1 and WWTP 2, the reactor used was constructed of CPVC pipe of 2 inch nominal diameter, and was approximately 3-4 inches long. This was placed within a water flow pipe having a nominal diameter, in the expanded section, of 4 inches (before and after which, the water pipe diameter was 2 inches). This carrier water was set to 15 gpm. The chemical reactant feed pump was set at approximately 40-50 strokes per minute, with a per stroke volume about 0.8 mL. The sodium bisulfate stock was approximately 30% technical grade solution, the sodium chlorite stock solution was approximately 18%, and the sodium hypochlorite nominal concentration was between about 4 and 12.5%. The wastewater stream being treated averaged about 1.8 MGD.

When the actual side stream pilot began, the flow rates of chemicals to the reactor of the present invention was set to achieve a complete fecal coliform kill, which was based on data from previous post clarifier testing. At this time, samples were taken from the 2-minute and the 5-minute contact point in the replicated contact chamber. These samples were studied for their disinfection characteristics and for their fecal coliform kill. Although most of the samples tested confirmed effective kills, some of the samples did not. It became apparent that bacterial count varied dramatically during the day and would require different dosing levels to maintain complete fecal kills during the wastewater disinfection process. This same phenomenon occurs with the existing chlorine dosing system and hourly corrections are made based on the variable disinfection demands. The same would be done with the $ClO_2$.

As various dosing rates were studied for their effectiveness in fecal coliform kill, it was noted that the lower dosing rates required more than 2 minutes for a complete fecal kill. For this reason, all samples were then taken from the 5-minute sampling point of the contact chamber.

Since the object of this pilot was to determine the effectiveness of the $ClO_2$, several strengths of the chlorite solution (CLO2 precursor) were next evaluated. Ultimately, a 10% solution was used only because of the sheer volume of chemical required to generate the same amount of $ClO_2$. For example, 1% would require 10 gallons and 5%, 2 gallons and so on.

From the materials handling standpoint, and issues relating to the toxicity there seemed to be greater consistency in the levels of $ClO_2$ generated with lower unreacted lo chlorite than by the more saturated chlorite solutions. Table 1(a through d) shows a sampling of the data obtained. Of the first 15 samples, 5 were taken at increasing percentages of the chlorite solutions. Here only the pH and kill rates were observed. At the time these 15 samples were taken, fecal coliform counts on the post clarifier water were not performed. It was, however, taken on subsequent samplings.

Table 1(a) illustrates the results of the testing done with differing solutions. The $ClO_2$ dose rate was maintained at 3.0 mg/ltr.

PPM Dose Rates and 5 Minute Contact Time

TABLE 1(a)

| Jan. 24, 2001 | Fecal Coliform (#cfu/100 mls) - Membrane Filter SM 9222D | | | |
|---|---|---|---|---|
| 5 minute contact | 1% | 2% | 5% | Clar. (untreated) |
| pH | 7.13 | 7.07 | 7.05 | 7.31 |
| Sample 1 | 35 | 22 | <1 | NA |
| Sample 2 | <1 | 27 | <1 | NA |
| Sample 3 | <1 | <1 | <1 | NA |
| Sample 4 | 34 | 25 | <1 | NA |
| Sample 5 | <1 | <1 | <1 | NA |

Tables 1(b, c, d) illustrate the fecal kills at the variable dose rates along with the pH and the residual at the 5 minute contact time mark.

TABLE 1(b)

Feb. 5, 2001

| | Fecal Coliform (#cfu/100 mls) - Membrane Filter SM 9222D Injector ppm | | | | |
|---|---|---|---|---|---|
| | 1.8 ppm | 2.23 ppm | 3.0 ppm pH | 3.97 ppm | 5.0 ppm |
| | 7.30 | 7.30 | 7.30 | 7.30 | 7.30 |
| 5 min. CLO2 residual | 1.29 | 1.32 | 1.39 | 1.60 | 1.40 |
| Sample 1 | <1 | <1 | <1 | <1 | 1 (*) |
| Sample 2 | <1 | <1 | <1 | <1 | <1 |
| Sample 3 | <1 | <1 | <1 | <1 | 1 (*) |
| Sample 4 | <1 | <1 | <1 | <1 | <1 |

It was noted that bits of algae were visually observed in these samples. It should be noted that even with higher dosing, some fecal coliform was detected in these samples that contained floating algae particles. It was first thought that the $ClO_2$ was not being completely neutralized. Additional sodium thiosulfate was added to samples 1 and 3 each day, and these samples were allowed an additional 20 minutes for dechlorination. There were, however, no discernible differences in these samples. It was also noted that the levels of residual $ClO_2$ in these samples varied dramatically. It is believed that this was the result of biological loading that results from the variable day-to-day conditions in the plant's treatment process.

TABLE 1(c)

Feb. 6, 2001

| | Fecal Coliform (#cfu/100 mls) - Membrane Filter SM 9222D | | | | |
|---|---|---|---|---|---|
| | 1.8 ppm | 2.23 ppm | 3.0 ppm pH | 3.97 ppm | 5.0 ppm |
| | 7.20 | 7.20 | 7.20 | 7.20 | 7.20 |
| 5 min. CLO2 residual | 1.60 | 1.37 | 1.59 | 1.41 | 1.77 |
| Sample 1 | <1 | <1 | <1 | <1 | <1 |
| Sample 2 | <1 | <1 | <1 | <1 | <1 |
| Sample 3 | <1 | <1 | <1 | <1 | <1 |
| Sample 4 | <1 | <1 | <1 | <1 | <1 |

TABLE 1(d)

Feb. 7, 2001

| | Fecal Coliform (#cfu/100 mls) - Membrane Filter SM 9222D | | | | |
|---|---|---|---|---|---|
| | 1.8 ppm | 2.23 ppm | 3.0 ppm pH | 3.97 ppm | 5.0 ppm |
| | 7.20 | 7.20 | 7.20 | 7.20 | 7.20 |
| 5 min. CLO2 residual | 0.52 | 0.07 | 0.97 | 1.63 | 1.88 |
| Sample 1 | <1 | <1 | <1 | <1 | <1 |
| Sample 2 | <1 | <1 | <1 | <1 | <1 |
| Sample 3 | <1 | <1 | <1 | <1 | <1 |
| Sample 4 | <1 | <1 | <1 | <1 | <1 |

Based upon the results of the above tables, fecal coliform is effectively killed at the lower dosing rate of 1.8 ppm. Further testing showed these kills were also achieved at dosing rates as low as 0.075 ppm. It should also be noted that residual levels of $ClO_2$ continued to decline over the balance of the contact and aeration time. The reasons for the monitoring of the fecal kills at the 5-minute mark resulted from the studies performed by C. Ruzic, "Chlorine dioxide-based water treatment in the food industry, 1996," which is illustrated in Table 2. The table represents a fecal kill with 0.15 ppm in 300 seconds and a similar kill with 0.25 ppm in 60 seconds.

With the myriad of constituents in the wastewater and the indiscriminate nature of the $ClO_2$ to oxidize many of these compounds, it was felt that with 1.0 ppm and 5 minutes contact time, the bacterial kill could occur.

TABLE 2

Bacterial Reduction Using Chlorine Dioxide (from C. Ruzic, 1996)

| Micro-organisms | ppm of $ClO_2$ | Contact Time (s) | Inactivation in % |
|---|---|---|---|
| Staphylococcus aureus | 1 | 60 | 99.999 |
| Eschericia Coli | 0.15 | 300 | 99.9 |
| Eschericia Coli | 0.25 | 60 | >99.999 |

TABLE 2-continued

Bacterial Reduction Using Chlorine Dioxide (from C. Ruzic, 1996)

| | | | |
|---|---|---|---|
| Streptococcus | 1 | 15 | >99.999 |
| Lactobacillus Brevis | 0.15 | 300 | 99.9 |
| Lactobacillus Brevis | 1 | 300 | >99.999 |
| Pseudomonas aeruginosa | 1 | 60 | >99.999 |

Fungicidal Activity of Chlorine Dioxide

| Micro-organisms | ppm of $ClO_2$ | Contact Time (min) | Inactivation in % |
|---|---|---|---|
| Saccharomyces diastaticus (yeast) | 0.15 | 10 | 99.9 |
| Saccharomyces diastaticus (yeast) | 1 | 1 | >99.999 |
| Saccharomyces diastaticus (yeast) | 0.5 | 10 | >99.999 |
| Saccharomyces diastaticus (yeast) | 1 | 1 | >99.999 |
| Penicillum expansum (mould) | 0.5 | 60 | 99.99 |
| Penicillum expansum (mould) | 2 | 20 | 99.999 |
| Pediococcus Damnosus (yeast) | 0.15 | 20 | 99.99 |
| Pediococcus Damnosus (yeast) | 0.3 | 5 | 99.99 |

TABLE 2-continued

Bacterial Reduction Using Chlorine Dioxide (from C. Ruzic, 1996)

| | | | |
|---|---|---|---|
| Pediococcus Damnosus (yeast) | 1 | 5 | 99.999 |
| Pectinatus cervisiiphilus (yeast) | 0.1 | 5 | 99.9 |

After numerous tests demonstrating fecal coliform kills with low residuals, we attempted our first bioassay with the organisms required for the Marine Surface Discharge Permit. *Mysidopsis bahia* (Mysids) and *Menidia beryllina* (Silversides) were subjected to $ClO_2$ treated effluent in these tests. Adequate volumes of chemical were brought to the site to conduct a dosing of the side stream for a 24-hour period. During this period, 2 gallons of treated water were taken at 6-hour intervals, preserved on ice and shipped to an independent bioassay laboratory (designated Independent Bioassay Laboratory A).

The results of this bioassay are depicted in Table 3a, b, and c. See the attachments, TABLE 3(a)

Initial Bio Assay Results
From Independent Bioassay Laboratory A
*Mysid* Shrimp

*Mysid bahia*

| | pH I | pH 48 hr | pH 48 hr (R) | pH 96 hr | Salinity | Salinity 48 hr | D.O. (I) Units | D.O. 48 hr | D.O. 48 hr (R) | D.O. 96 hr | Cond | Hard. | Alk. |
|---|---|---|---|---|---|---|---|---|---|---|---|---|---|
| | S.U. | S.U. | S.U. | S.U. | ppt | ppt | mg/l | mg/l | mg/l | mg/l | umhos | mg/l | mg/l |
| Control | 8.09 | 8.06 | 7.42 | 7.73 | 21.7 | 21.2 | 6.2 | 3.9 | 6.1 | 4.5 | NA | NA | Na |
| Sep. 3, 2001 12:00 | 7.85 | 7.83 | 7.82 | | 20.0 | 19.9 | 5.8 | 2.6 | 6.5 | | 1600 | 300 | 100 |
| Sep. 3, 2001 18:00 | 7.94 | 7.88 | 7.95 | | 20.8 | 20.7 | 5.7 | 3.4 | 6.2 | | 1500 | 300 | 110 |
| Sep. 3, 2001 24:00 | 7.87 | 7.81 | 7.87 | | 29.3 | 19.1 | 5.7 | 3.0 | 6.4 | | 1500 | 300 | 100 |
| Sep. 4, 2001 06:00 | 7.87 | 7.82 | 7.82 | | 19.6 | 19.5 | 5.8 | 2.2 | 6.4 | | 1500 | 300 | 110 |

PH (I) is the initial pH, pH at the 48-hour mark, pH (R) after the renewal, pH at the 96-hour mark. Salinity is indicated in parts per thousand initially at the 48-hour mark. Dissolved oxygen initially (I), at the 48-hour mark, after the renewal (R) and at the 96-hour mark. Cond. stands for conductivity in microhms. Hard. stands for hardness as CaCO3. Alk. is alkalinity.

TABLE 3(b)

Water Quality Parameters in Bioassay using silverside minnow test organism.

*M. beryllina*

| | pH I | pH 48 hr | pH 48 hr (R) | pH 96 hr | Salinity | Salinity 48 hr | D.O. (I) | D.O. 48 hr | D.O. 48 hr (R) | D.O. 96 hr |
|---|---|---|---|---|---|---|---|---|---|---|
| Control | 8.09 | 8.06 | 7.61 | 7.76 | 21.7 | 21.2 | 6.2 | 4.6 | 6.1 | 5.2 |
| Sep. 3, 2001 12:00 | 7.85 | 7.83 | 7.91 | 8.01 | 20.0 | 19.9 | 5.8 | 3.8 | 6.5 | 4.4 |
| Sep. 3, 2001 18:00 | 7.94 | 7.88 | 7.86 | 7.94 | 20.8 | 20.7 | 5.7 | 3.5 | 6.2 | 3.4 |
| Sep. 3, 2001 24:00 | 7.87 | 7.81 | 7.85 | 7.97 | 19.3 | 19.1 | 5.7 | 3.7 | 6.4 | 3.9 |
| Sep. 4, 2001 06:00 | 7.87 | 7.82 | 7.87 | 7.90 | 19.6 | 19.5 | 5.8 | 3.6 | 6.4 | 3.6 |

TABLE 3(c)

Survival Data at end of 96-hour test period for both test species.

| Percent Survival | Mysid bahia | m. beryllina |
|---|---|---|
| Control | 100% | 100% |
| Sep. 3, 2001 12:00 | 0% | 95% |
| Sep. 3, 2001 18:00 | 0% | 95% |
| Sep. 3, 2001 24:00 | 0% | 95% |
| Sep. 4, 2001 06:00 | 0% | 100% |

Table 3(c) illustrates the survivability of the organisms at the 96-hour end-point in the test for each of the 4 samples taken (samples indicated by date and time each sample was taken.).

While the survival of the silverside minnow, M. beryllina, was positive, the failure of the Mysid was disappointing. Obviously, additional testing would be necessary to determine why the Mysid failed to survive. It was decided that we should take samples under the parameters run at wastewater plants, such as total suspended solids (TSS), total Kjedahl Nitrogen (TKN), carbonaceous biological oxidation demand (CBOD5), in addition to the fecal coliforms. Table 4 gives comparison data for the above-mentioned parameters. Side stream samples and the actual plant samples were taken simultaneously for direct comparison and evaluation. Five samples of each location were taken in succession to have as a broad base for comparison. FIGS. 7 and 8 depict sample locations.

Table 4 demonstrates these results. Our observations did not illustrate any significant or potentially harmful differences.

TABLE 4

| Jan. 24, 2002 | TKN | TSS | CBOD5 |
|---|---|---|---|
| PH 6.5 | | | |
| Sample 1 (ClO2) | 5.88 | 3.6 | 5.8 |
| Sample 2 (ClO2) | 6.02 | 3.2 | 5.6 |
| Sample 3 (ClO2) | 6.16 | 3.2 | 5.8 |
| Sample 4 (ClO2) | 6.16 | 3.6 | 6.0 |
| Sample 5 (ClO2) | 6.02 | 4.0 | 5.4 |
| PH 7.2 | | | |
| Sample 6 (Cl2/SO2) | 6.06 | 3.2 | 5.0 |
| Sample 7 (Cl2/SO2) | 6.16 | 3.2 | 5.5 |
| Sample 8 (Cl2/SO2) | 5.88 | 3.6 | 5.5 |
| Sample 9 (Cl2/SO2) | 6.16 | 2.8 | 6.0 |
| Sample 10 (Cl2/SO2) | 6.16 | 3.6 | 6.0 |

A complete in-house water analysis was then taken on a composite of the plant's post clarifier effluent to determine if there were any potential compounds present in the water that would lead to the toxicological issues that killed the Mysid shrimp. In the interest of economics, the protocol for the required bioassays was obtained and the next several bioassays were conducted in Bioassay Lab 2. Numerous variables were tested and their performance evaluated. In the interest of accurately determining the agent or agents responsible for the demise of the shrimp, several outside experts were consulted for their opinions.

After performing numerous in-house tests on both the Mysids and the Silversides, its found that the Silversides always survived the post $ClO_2$ dosing. Based on this, the focus was directed toward the successful mysid shrimp survival during the standard mysid shrimp acute bioassay.

After close monitoring of the free chlorine, total chlorine ammonias, chlorites, chlorine dioxide residuals, and making adjustments to our chlorine dioxide generator, successful (acceptable end-point survival) mysid shrimp bioassay were repeatability obtained. Accurate $ClO_2$ precursor chemical mixing was watched to assure as complete a conversion of chlorite to $ClO_2$. The plant was also monitored to assure it's proper function and specifically the $NH_3$ levels. We had concluded that when we forced our reaction with too much hypochlorite chloramines, as a result of the ammonia level, were generated so we utilized a weaker hypochlorite solution in driving our reaction.

Having accomplished successful bioassays in side stream testing, a full-scale pilot evaluation was initiated. This received approval of the relevant regulatory authorities. However, due to required repair of certain physical components at WWTP one, this pilot evaluation was conducted at a second WWTP, designated WWTP 2. WWTP 2 was of approximately the same size as WWTP 1, operated under much the same criteria, and discharged much of its effluent into a marine estuarine water body and therefore also had mysid shrimp and silverside minnows as the bioassay test species. Discussion and results of the pilot evaluation at WWTP 2 are provided in Example 6, below.

EXAMPLE 6

After moving the $ClO_2$ generator WWTP 2, a full-scale pilot was conducted which disinfected the plant's total post clarifier volume. Again, the $ClO_2$ disinfection system operated under actual operational variables with the same successful results. Testing showed the effluent treated with $ClO_2$ met or exceeded the desired disinfectant levels. The presence of possible toxicological residuals was also tested by placing mysid shrimp and silverside minnows into the post treated effluent. Both Laboratory 2, previously used, and Laboratory 3, an independent laboratory in the region, did this testing.

Results from both laboratories showed that the marine organisms subjected to $ClO_2$ treated effluent had high rates of survivability.

Baseline chemical and bacteriological testing a WWTP 2 revealed a similarity with WWTP 1 with the exception of the post clarifier bacterial counts. WWTP 1 averaged a count of 18,000 cfus/100 ml, while the WWTP 2 had an average of 8,500 cfus/100 ml. This was determined to be the result of the improved aeration process (by diffused air) resulting in an improved nitrogen cycle.

The ammonia levels at this plant seldom exceeded 0.2 p/ml and the chloramine formation was considerably less. To establish a base line on this plants performance water samples were analyzed and reviewed.

The plant's performance on the existing sodium hypochlorite system indicated by the following parameters: pH, total residual chlorine and the fecal coliform counts can be seen in Table 5(a-c).

Clarifier Sample points 1 through 4 are the following: 1 is at the beginning of the chlorine contact chamber, 2 is at the mid-point of the chamber, 3 is at the end of the chamber and 4 is at the aeration basin. TNTC=too numerous to count Wednesday 31 Jul. 2002

TABLE 5(a)

| PH | Noon | 1:00 pm |
|---|---|---|
| Clarifier sample | 7.48 | 6.88 |
| Sample point 1 | 7.26 | 6.95 |
| Sample point 2 | 7.22 | 6.95 |
| Sample point 3 | 7.21 | 6.95 |
| Sample point 4 | 7.22 | 7.05 |

TABLE 5(b)

| TRC | Noon | 1:00 pm |
|---|---|---|
| Clarifier sample | 0.0 | 0.0 |
| Sample point 1 | 2.19 | 2.01 |
| Sample point 2 | 1.61 | 1.52 |
| Sample point 3 | 0.96 | 0.88 |
| Sample point 4 | 0.04 | 0.02 |

TABLE 5(c)

| Fecal coliform | Noon | 1:00 pm |
|---|---|---|
| Clarifier sample | TNTC | TNTC |
| Sample point 1 | 1 | 4 |
| Sample point 2 | 0 | 4 |
| Sample point 3 | 0 | 45 |
| Sample point 4 | 6 | 78 |

A chlorine dioxide reactor of the present invention, with all needed supply tanks, feed lines and pumps, was set up at the WWTP 2 in much the same position as it was at WWTP 1 (post clarifier at the contact chamber). The point of the $ClO_2$ injection is referred to as the Parchall flume. Here, the water leaving the clarifiers enters a chamber and spills over through the narrowing Parchall flume where the $ClO_2$ is mixed into the water.

In an effort to have a reference point for the toxicity, additional testing of the water with both the disinfectants being employed is demonstrated in the following Tables 6(a, b). The results of that analytical review are available at the end of this study as an attachment.

TABLE 6(b)

| | B | C | BDC | CDB | TTHMS |
|---|---|---|---|---|---|
| | | | UNITS | | |
| | UG/L | UG/L | UG/L | UG/L | UG/L |
| CLAR | <1.0 | <1.0 | <1.0 | <1.0 | <1.0 |
| CL2/SO2 | 8.5 | 31 | 41 (*) | 44 (*) | 124.5 |
| 14:00 1 | NA | NA | NA | NA | NA |
| 14:00 2 | NA | NA | NA | NA | NA |
| 14:00 3 | NA | NA | NA | NA | NA |
| 14:00 4 | 2.8 | 7.5 | 9.8 | 12 | 32.1 |
| 15:00 1 | NA | NA | NA | NA | NA |
| 15:00 2 | NA | NA | NA | NA | NA |
| 15:00 3 | NA | NA | NA | NA | NA |
| 15:00 4 | NA | NA | NA | NA | NA |

B = Bromoform,
C = Chloroform,
BDC = Bromodichloromethane,
CDB = Chlorodibromomethane,
TTHMS = (Total THMS)
Clar-B, BDC, CDB were not detected,
(*) exceed the surface water limits An outside laboratory certified by NELAC conducted additional testing for the following water quality parameters. The results of that testing is also indicated in Tables 6(a, b).

TOC(Total Organic Carbon), E415.1, TKN(Total Kjedahl Nitrogen), E351.2, NH3(Ammonia), E350.1, TRP(Total Recoverable Phenolics), E420.4, TP(Total Phosphorous), E365.4, Cu(Copper), E220.2, Hg(Mercury), E245.1, Ni(Nickel), E249.2, Ag(Silver), E272.2, Clo2-(Chlorite), E300.1, Clo3-(Chlorate). E300.1

After evaluating the testing results and finding no compounds that we considered lethal to the Mysids, an in-house TABLE 6(a)

MONDAY Aug. 12, 2002

CLARIFIER AT 11:00 CL2/SO2 AT 11:15 CLO2 AT 14:00 CLO2 15:00

| UNITS | pH S.U. | Free CL MG/L | CLO2 MG/L | NH3 MG/L | DO MG/L | TRC MG/L | TOC MG/L | TKN MG/L | NH3 MG/L |
|---|---|---|---|---|---|---|---|---|---|
| CLAR | 7.0 | 0.00 | NA | 0.00 | 6.00 | 0.00 | 10 | 1.5 | 0.14 |
| CL2/SO2 | 7.0 | 0.01 | NA | 0.00 | 7.00 | 0.01 | 10 | 1.3 | 0.17 |
| 14:00 1 | 6.6 | 0.03 | 0.05 | 0.00 | 7.0 | 0.27 | NA | NA | NA |
| 14:00 2 | 6.61 | 0.03 | 0.04 | NA | 7.0 | 0.22 | NA | NA | NA |
| 14:00 3 | 6.6 | 0.00 | 0.03 | NA | 7.2 | 0.17 | NA | NA | NA |
| 14:00 4 | 6.62 | 0.02 | 0.03 | NA | 7.8 | 0.05 | 10 | 1.3 | 0.13 |
| 15:00 1 | 6.60 | 0.01 | 0.04 | NA | 7.0 | 0.14 | NA | NA | NA |
| 15:00 2 | 6.62 | 0.00 | 0.03 | NA | 7.0 | 0.12 | NA | NA | NA |
| 15:00 3 | 6.62 | 0.00 | 0.03 | NA | 7.1 | 0.10 | NA | NA | NA |
| 15:00 4 | 6.62 | 0.01 | 0.03 | NA | 7.8 | 0.05 | NA | NA | NA |

| UNITS | ORG N MG/L | TRP MG/L | TP MG/L | CU UG/L | HG UG/L | NI UG/L | AG UG/L | CLO2- MG/L | CLO3- MG/L |
|---|---|---|---|---|---|---|---|---|---|
| CLAR | 1.4 | ND | 2 | 1.5 | ND | 09 | 0.12 | ND | 0.16 |
| CL2/SO2 | 1.1 | NA | 1.2 | 1.8 | ND | 0.86 | 0.12 | ND | 1.2 |
| 14:00 1 | NA | NA | NA | NA | NA | NA | NA | NA | NA |
| 14:00 2 | NA | NA | NA | NA | NA | NA | NA | NA | NA |
| 14:00 3 | NA | NA | NA | NA | NA | NA | NA | NA | NA |
| 14:00 4 | 1.2 | ND | 2.3 | 1.7 | .057 | 0.08 | 0.12 | 0.66 | 0.86 |
| 15:00 1 | NA | NA | NA | NA | NA | NA | NA | NA | NA |
| 15:00 2 | NA | NA | NA | NA | NA | NA | NA | NA | NA |
| 15:00 3 | NA | NA | NA | NA | NA | NA | NA | NA | NA |
| 15:00 4 | NA | NA | NA | NA | NA | NA | NA | NA | NA | bioassay was scheduled. On the 14 of Aug. 2002, 4 water grabs were taken at 6-hour intervals. The lab was set up to receive the water and perform the bioassay. Here again, because of the continued survivability of the silverside minnows, we elected to conduct the testing using only the Mysids.

Duplicate bowls containing ten Mysid shrimp per bowl were set up as samples to test survivability. These were in 100% Effluent. We also set up bowls of shrimp in the raw clarifier sample as well as the plant's CL2/SO2 Effluent. As the results of this bioassay show in Table 7, we experienced disappointing losses. Afterwards, when consulting the plant's operators, we discovered that several thousand gallons of landfill leachate had been introduced into the system approximately 8-10 hours before. Although accepting landfill leachate is a normal practice, it is generally trickled into the systems headworks. This large slug of unqualified effluent required the bioassay test to be repeated. The resulting data of the failed in-house bioassay is indicated in Table 7.

In addition to the dosing rates illustrated in Table 8, the results of the bioassay are indicated in Table 9.

While not depicted in this table, a control group was also established with the 100% survivability of Mysids. All tests were conducted in duplicate. It was decided that these tests should be conducted with dilutions of 100%, 75%, 50% and 25% in the event of Mysid mortality.

Dissolved oxygen (DO), temperature, and pH were monitored. Here we also included several sample bowls of Mysids and fed them with live *Artemia* (brine shrimp) as well as a dried ground sliiimp. Ammoniia levels in the above sample bowls were also monitored. Although there was no significant difference noted between the uses of live brine shrimp and dried food as far as the survival of the shrimp was concerned, a slight escalation of the ammonia was noted in the use of the live food. The survival rate of the Mysid shrimp less the ammonia data, are indicated in Table 9.

TABLE 7

SET UP Aug. 13, 2002
No. of surviving shrimp

|  | SAL | PH | DO | INITIAL DAY 1 | DAY 2 | DAY 3 | DAY 4 | % SURV | AVG |
|---|---|---|---|---|---|---|---|---|---|
| CLAR | 20.5 | 6.65 | 6.5 | 10 | 5 | 1 | 0 | 0 |  |
| CL2/SO2 | 20 | 8.3 | 6.6 | 10 | 9 | 9 | 9 | 90% |  |
| 14:00 A | 20 | 8.18 | 7.8 | 10 | 6 | 3 | 0 | 0% |  |
| 14:00 B | 20 | 8.21 | 7.9 | 10 | 10 | 9 | 8 | 80% | 40% |
| 15:00 A | 20 | 8.23 | 7.8 | 10 | 10 | 9 | 6 | 60% |  |
| 15:00 B | 20 | 8.20 | 7.9 | 10 | 9 | 8 | 2 | 20% | 40% |

The entire water sampling and the bioassays were repeated on the 19 Aug. 2002. The result of that bioassay is indicated in Tables 8 and 9.

TABLE 8

|  |  | NH3 (MG/L) | PH (S.U.) | TRC (MG/L) | FECAL |  |  |
|---|---|---|---|---|---|---|---|
| 11:00 AM | CLAR | 0.00 | 7.20 | 0.01 | 27,000 |  |  |
| 11:00 AM | CL2/SO2 | 0.00 | 7.40 | 0 | 6 |  |  |
|  |  |  | 315 | CLO2 (MG/L) | CL2 (MG/L) | TRC (MG/L) | FECAL |
| 13:00 1.2 PPM DOSE RATE |  |  | 1 | 0.05 | 0.02 | 0.25 | 6 |
| 100% SETTING ON PUMP 1 |  |  | 2 |  |  |  |  |
|  |  |  | 3 |  |  |  |  |
|  |  |  | 4 |  |  |  |  |
|  |  |  | CLAR |  |  |  | 11,000 |
| 15:00 1.3 MG |  |  | 155 | CLO2 | CL2 | TRC | FC |
| 0.91 PPM DOSE |  |  | 1 | 0.04 | 0.02 | 0.09 |  |
| PUMP AT 50% |  |  | 2 | 0.04 | 0.02 | 0.14 |  |
|  |  |  | 3 | 0.04 | 0.04 | 0.12 |  |
|  |  |  | 4 | 0.03 | 0.03 | 0.05 | 15 |
|  |  |  | CLAR |  |  |  | 3,000 |
| 15:45 1.03 MG |  |  | 110 | CLO2 | CL2 | TRC |  |
| 1.05 PPM DOSE RATE |  |  | 1 | 0.06 | 0.01 | 0.13 |  |
| PUMP AT 50% |  |  | 2 | 0.1 | 0.02 | 0.11 |  |
|  |  |  | 3 | 0.03 | 0.02 | 0.12 |  |
|  |  |  | 4 | 0.06 | 0.01 | 0.05 | 26 |
|  |  |  | CLAR |  |  |  | 12,500 |

TABLE 9

The survival rate of *Mysid* Shrimp in diluted solutions of 100, 75, 50, and 25%
SET UP 10 AM Aug. 20, 2002

| TOXICITY | (INITIAL) A | B | PH | DO | DAY 1 A | B | PH | DO | DAY 2 A | B | PH | DO | DAY 3 A | B | PH | DO |
|---|---|---|---|---|---|---|---|---|---|---|---|---|---|---|---|---|
| 1.05 PPM DOSE | | | | | | | | | | | | | | | | |
| 100% | 10 | 10 | 8.2 | 8.0 | 10 | 10 | 8.1 | 7.6 | 9 | 10 | 8.1 | 7.8 | 8 | 10 | 8.1 | 6.9 |
| 75% | 10 | 10 | 8.2 | 8.0 | 10 | 10 | 8.0 | 7.5 | 10 | 10 | 8.1 | 7.9 | 10 | 10 | 8 | 6.8 |
| 50% | 10 | 10 | 8.2 | 8.0 | 10 | 10 | 8.1 | 7.5 | 10 | 10 | 8.1 | 7.8 | 10 | 9 | 8.1 | 6.9 |
| 25% | 10 | 10 | 8.1 | 7.9 | 10 | 10 | 8.0 | 7.5 | 10 | 10 | 8.1 | 7.9 | 10 | 10 | 8.1 | 6.9 |
| 0.64 PPM DOSE | | | | | | | | | | | | | | | | |
| 100% | 10 | 10 | 8.2 | 8.0 | 10 | 10 | 8.0 | 7.5 | 10 | 10 | 8.1 | 7.9 | 7 | 10 | 8.1 | 6.9 |
| 75% | 10 | 10 | 8.2 | 8.0 | 10 | 10 | 8.0 | 7.6 | 10 | 10 | 8.1 | 7.8 | 9 | 10 | 8 | 6.8 |
| 50% | 10 | 10 | 8.1 | 7.9 | 10 | 10 | 8.0 | 7.6 | 10 | 10 | 8.1 | 7.9 | 10 | 10 | 8 | 6.8 |
| 25% | 10 | 10 | 8.2 | 8.0 | 10 | 10 | 8.0 | 7.5 | 10 | 10 | 8.1 | 7.8 | 9 | 9 | 8 | 6.9 |
| CL2SO2 | 10 | 10 | 8.2 | 8 | 10 | 10 | 8.2 | 7.6 | 10 | 10 | 8.1 | 7.9 | 10 | 10 | 8.1 | 6.9 |

| TOXICITY | DAY 4 A | B | PH | DO | 24 HR | 48 HR | 72 HR | 96 HR |
|---|---|---|---|---|---|---|---|---|
| 1.05 PPM DOSE | | | | | | | | |
| 100% | 6 | 8 | 8.2 | 6.4 | 100 | 100 | 90 | 70 |
| 75% | 10 | 9 | 8.1 | 6.5 | 100 | 100 | 100 | 95 |
| 50% | 9 | 10 | 8.2 | 6.4 | 100 | 100 | 95 | 95 |
| 25% | 10 | 10 | 8.1 | 6.3 | 100 | 100 | 100 | 100 |
| 0.64 PPM DOSE | | | | | | | | |
| 100% | 5 | 9 | 8.1 | 6.4 | 100 | 100 | 85 | 70 |
| 75% | 8 | 10 | 8.1 | 6.4 | 100 | 100 | 95 | 90 |
| 50% | 10 | 10 | 8.2 | 6.4 | 100 | 100 | 100 | 100 |
| 25% | 9 | 9 | 8.1 | 6.3 | 100 | 100 | 90 | 90 |
| CL2SO2 | 10 | 10 | 8.2 | 6.4 | | | | |

With the success of the above bioassay series that began on Aug. 20, 2002, it was concluded that a third party test was needed to verify research data. Water grabs from the Anastasia Island Treatment Facility, taken on Aug. 28, 2002, were delivered to Laboratory 4, an independent bioassay laboratory. Additional testing of the water sent to Laboratory 4 labs was also forwarded to another contract lab to document the water quality during the sample periods for the bioassays. It should be noted here that the plant was operating under their normal operating conditions and accepting both landfill leachate as well as septic tank and portable toilet waste. These were however pumped into a storage tank and then trickled into the influent stream at the headworks.

These results are illustrated in table 10.

Table 10 is a summary of water quality during the bioassay period

Tables 11, 12 are summaries of the results of the bioassay data from Laboratory 4. The complete toxicological study as reference is included as attachment at the end of this study.

Table 11 is a summary of the Toxicity data from Laboratory 4

| Sample date and time | *M. beryllina* % survival |
|---|---|
| Control | 100 |
| Aug. 28, 2002 10:15 | 100 |
| Aug. 28, 2002 16:00 | 100 |
| Aug. 28, 2002 22:00 | 100 |
| Aug. 29, 2002 09:30 | 100 |

Table 12 Summary data from Laboratory 4

| 28-Aug UNITS | TIME | PH S.U. | PH (1) S.U. | NH3 MG/L | NH3 (1) MG/L | CLO2 MG/L | CL2 MG/L | TRC MG/L | TRC (1) MG/L | FECAL | CLO3- (2) MG/L | CL02- (2) MG/L | COND(1) UOHMS | ALK(1) MG/L |
|---|---|---|---|---|---|---|---|---|---|---|---|---|---|---|
| CLAR | 8:30 | 7.16 | NA | 0.17 | NA | NA | NA | NA | NA | 12,000 | NA | NA | NA | NA |
| CL2SO2 | 8:30 | 7.17 | NA | 0.33 | NA | NA | 0.01 | 0.01 | NA | 55 | NA | NA | NA | NA |
| CLO2 | 10:15 | 7.16 | 7.6 | 0.21 | 0.02 | 0.07 | 0.01 | 0.01 | 0.08 | 45 | 1600 | <0.1 | 1750 | 25 |
| CLO2-1 | 12:30 | NA | NA | NA | NA | 0.09 | NA | NA | NA | NA | NA | NA | NA | NA |
| CLO2-4 | 12:30 | NA | NA | NA | NA | 0.06 | 0.05 | 0.09 | NA | NA | NA | NA | NA | NA |
| CLAR | 16:00 | 7.20 | NA | 0.11 | NA | NA | NA | NA | NA | NA | NA | NA | NA | NA |
| CLO2 | 16:00 | 7.21 | 7.5 | 0.17 | 0.07 | 0.06 | 0.04 | 0.06 | 0.1 | NA | 700 | <0.1 | 1650 | 25 |
| CLAR | 22:00 | 7.15 | NA | 0.10 | NA | NA | NA | NA | NA | NA | NA | NA | NA | NA |
| CLO2 | 22:00 | 7.18 | 7.8 | 0.13 | 0.01 | 0.06 | 0.04 | 0.06 | 0.07 | NA | 630 | <0.1 | 1620 | 25 |
| CLO2 | 9:30 | 7.22 | 7.5 | NA | 0.01 | 0.04 | 0.02 | 0.02 | 0.04 | NA | 1300 | <0.1 | 1575 | 25 |

TABLE 12

Summary data from Laboratory 4

Sample survival % of *M. bahia*

| % Effluent | Aug. 28, 2002 10:15 | Aug. 28, 2002 16:00 | Aug. 28, 2002 22:00 | Aug. 29, 2002 09:30 |
|---|---|---|---|---|
| Control | 100 | 100 | 100 | 100 |
| 6.25 | 100 | 100 | 100 | 100 |
| 12.5 | 95 | 100 | 100 | 100 |
| 25 | 100 | 100 | 100 | 100 |
| 50 | 95 | 100 | 100 | 100 |
| 100 | 100 | 100 | 100 | 100 |

With the successful bioassay conducted by the Laboratory 4 labs, a second series of water samples was taken for the repeat bioassay. These samples were taken on Sep. 11, 2002 and forwarded to Laboratory 4 labs on Sep. 12, 2002 to conduct the bioassay. The results of this test for both the water quality toxicity and the bioassay are illustrated in the Tables 13, 14 and 15.

In summary, testing conducted by the Laboratory 2 and that of Laboratory 4 show that the present method of $ClO_2$ generation is a highly effective disinfectant, which meets or exceeds the requirements by wastewater facilities for bacterial control. Furthermore, there is no apparent residual toxicological effect on marine organisms that are subjected to this new method of wastewater disinfection.

WWTP 1 treats wastewater at one location. The plant is a 5.0 mgd AADF complete mix activated sludge wastewater treatment facility consisting of two (2) 1.2 mgd aeration basins, two (2) 0.76 mgal secondary clarifiers, with chlorine disinfection and de-chlorination. The permitted capacity has been 4.5 mgd, and is being changed to 4.950 mgd for the new permit period. Residuals are aerobically treated in two (2) 0.36 mgal sludge holding tanks, dewatered and hauled to several locations as Class B Sludge. The plant is capable of feeding 2,000 pounds per day (lbs/d) of chlorine, which is delivered and stored in one (1) ton steel cylinders. These cylinders are pressurized; therefore, the chlorine is mainly in the liquid state, with a gaseous headspace. The gaseous chlorine is drawn from the cylinder, piped to the chlorinator, dosed into the stream and maintained in the chlorine contact cham-

| 11-Sep UNITS | TIME | PH S.U. | PH (1) S.U. | NH3 MG/L | NH3 (1) MG/L | CLO2 MG/L | CL2 MG/L | TRC MG/L | TRC (1) MG/L | FECAL | CLO3- (2) MG/L | CLO2- (2) MG/L | COND (1) UOHM | ALK (1) MG/L | HRD (1) MG/L |
|---|---|---|---|---|---|---|---|---|---|---|---|---|---|---|---|
| CLAR | 10:00 | 7.07 | NA | 0.22 | NA | NA | NA | NA | NA | 6,000 | NA | NA | NA | NA | NA |
| CL2SO2 | 10:00 | 7.22 | NA | 0.26 | NA | NA | NA | NA | NA | 35 | NA | NA | NA | NA | NA |
| CLO2 | 10:00 | 7.24 | 7.6 | 0.17 | 0.06 | 0.06 | 0.03 | 0.05 | 0.07 | 53 | | | 1695 | 200 | 288 |
| CLAR | 15:30 | 7.04 | NA | NA | NA | NA | NA | NA | NA | NA | NA | NA | NA | NA | NA |
| CLO2 | 15:30 | 7.13 | 7.7 | NA | 0.02 | 0.06 | 0.02 | 0.07 | 0.09 | 155 | | | 1710 | 200 | 270 |
| CLAR | 22:00 | 7.00 | NA | NA | NA | NA | NA | NA | NA | NA | NA | NA | NA | NA | NA |
| CLO2 | 22:00 | 7.11 | 8.1 | NA | 0.16 | 0.06 | 0.03 | 0.06 | 0.07 | NA | | | 1780 | 190 | 280 |
| CLAR | 10:00 | 7.12 | NA | NA | NA | NA | NA | NA | NA | NA | NA | NA | NA | NA | NA |
| CLO2 | 10:00 | 7.13 | 7.60 | NA | 0.01 | 0.05 | 0.02 | 0.05 | 0.05 | NA | | | 1655 | 190 | 300 |

Tables 14 and 15 are summary data from Laboratory 4. The complete toxicological results are provided at the end of this study as attachments.

TABLE 14

Sample survival % of *M. berylina*

| % Effluent | Sep. 11, 2002 10:00 | Sep. 11, 2002 15:30 | Sep. 11, 2002 22:00 | Sep. 12, 2002 10:00 |
|---|---|---|---|---|
| Control | 100 | 100 | 100 | 100 |
| 6.25 | 100 | 100 | 100 | 100 |
| 12.5 | 100 | 100 | 100 | 100 |
| 25 | 100 | 100 | 100 | 95 |
| 50 | 95 | 100 | 100 | 100 |
| 100 | 95 | 100 | 100 | 100 |

TABLE 15

Sample survival % of *M. bahia*

| % Effluent | 9/11/02 10:00 | 9/11/02 15:30 | 9/11/02 22:00 | 9/12/02 10:00 |
|---|---|---|---|---|
| Control | 100 | 100 | 100 | 100 |
| 6.25 | 100 | 100 | 100 | 100 |
| 12.5 | 100 | 100 | 100 | 100 |
| 25 | 95 | 100 | 100 | 95 |
| 50 | 100 | 100 | 100 | 100 |
| 100 | 100 | 90 | 100 | 100 | ber where some is used within the plant and the rest is de-chlorinated with sulfur dioxide. The average design dosage for the facility is 0.5 to 1.0 mg/l (ppm) in the chlorine contact chamber and a de-chlorinated residual of 0.01 mg/l (ppm). This plant is permitted to surface discharge its final effluent into the Matanzas River (Class III Marine Waters).

WWTP 2 is described as a 4.0 mgd. AADF complete mix activated sludge wastewater treatment facility with chlorination disinfection, dechlorination and post aeration. The facility includes tertiary up flow filters to a 0.8 mgd. AADF for effluent for a part III (non restricted public access) reuse followed by chlorine injection to meet high-level disinfection requirements. Disinfection is accomplished using a sodium hypochlorite solution. Residuals are thickened with a belt thickener and stored in an aerobic digester prior to dewatering with a belt filter press.

The dewatered residuals are hauled to a regional residuals disposal facility. Recent instrumentation changes that have been implemented at the facility are the installation of a turbidimeter and a total chlorine analyzer at the secondary treatment contact chamber, a pH meter/analyzer at the secondary treatment aeration basin, and a total residual chlorine analyzer and pH meter/analyzer at the Marsh Creek Country Club Golf Course Reuse Pond.

This facility is permitted to surface discharge to the Matanzas River (Class III Marine Waters) and a slow-rate public access reuse (R001) system for the irrigation of the Marsh Creek Country Club Golf Course.

Objective

The objective of this study was to perform the necessary disinfection treatment of the post clarifier discharge, study post plant toxicological effects on specified marine organisms and ultimately develop an effective $ClO_2$ dosing strategy.

This dosing strategy must then result in the successful replacement of chlorine with chlorine dioxide while meeting the necessary disinfection guidelines without generating undesirable levels of THMs, HAAs, chlorites and chlorates, chloramines, free and total chlorine while passing the required marine bioassays.

Background

Chlorine has historically been the primary choice for disinfection of wastewater in the United States. The advantages to using chlorine are primarily cost, availability, and its known performance as a disinfectant. There are, however, certain drawbacks to the use of chlorine. Chlorine interacts with organic compounds present in wastewater to form undesirable disinfection byproducts THMs and HAAs. Many of these byproducts, such as chloroform, bromoform, di and tri chloro acetic acids, have carcinogenic properties and have been linked to potentially harmful long-term health effects. Chlorine's effectiveness is greatly diminished when it is used outside a narrow pH range (from pH 7-8). This can result in the over or under dosing of the effluent and generating greater levels of these undesirable byproducts or not effectively disinfecting the discharge.

There are also significant risk management issues associated with the transport, storage and maintenance of chlorine based disinfection systems.

Recently, as a result of the terrorist attacks on the United States, there is now also the additional threat of the use of chlorine gas as a potential terrorists weapon. Due to these performance concerns, risk factors, and stricter regulations regarding disinfection byproducts for surface water discharge and re-use water, alternatives to chlorine for use as a primary disinfectant are needed.

The recently concluded pilot study has produced encouraging results. Bio-Chem Resources' new method of $ClO_2$ generation is, a highly effective disinfectant that meets and exceeds the requirements of WWTP 1 and WWTP 2 for bacterial control in wastewater. Desired disinfectant levels were achieved and maintained over a wide range of operational variables that occurred at these facilities during testing periods. It should be noted, however, to achieve maximum benefit from chlorine dioxide disinfection (or any other disinfection process), a treatment plant needs to maintain good operational procedures. Disinfection by-products (THM's and HAA's) were also significantly reduced during these same test periods. Furthermore, repeated tests of subjecting marine organisms to the above $ClO_2$ treated effluents showed no toxicological effect.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A reactor for generation of chlorine dioxide, comprising:
a reaction chamber with an adjustable chamber volume;
a first inlet pipe and a second inlet pipe configured to communicate with the reaction chamber;
an exit pipe configured to communicate with the reaction chamber; and
a pressure activated discharge valve coupled to said exit pipe,
wherein the pressure activated discharge valve is configured to discharge chlorine dioxide generated by the reactor and is configured to regulate the pressure within the reaction chamber when the reactor is operating,
wherein the reaction chamber is defined by walls of a main body and an end piece, the main body having a threaded opening at one end, and the end piece being matingly threaded with the threaded opening, and
wherein the threaded opening is configured for adjustable positioning of the end piece within the main body, resulting in adjustment of the chamber volume.

2. The reactor of claim 1, wherein said discharge valve is positioned at an end of said exit pipe, and the reactor further comprises a discharge orifice at a discharge end of said discharge valve.

3. The reactor of claim 1, further comprising:
a first back-flow check valve coupled to the first inlet pipe; and
a second back-flow check valve coupled to the second inlet pipe.

4. The reactor of claim 1, further comprising a reactor body surrounding the reaction chamber.

5. The reactor of claim 4, further comprising a heater for heating said reactor.

6. The reactor of claim 5, further comprising an insulation placed between said reactor body and said reactor chamber, but not between said heater and said reaction chamber.

7. The reactor of claim 2, wherein said reactor is positioned within a flow channel into which the discharge orifice discharges chlorine dioxide.

8. The reactor of claim 2, wherein said reactor is positioned within a pipe into which the discharge orifice discharges chlorine dioxide.

9. The reactor of claim 1, further comprising a third inlet pipe configured to communicate with the reaction chamber.

10. The reactor of claim 9, further comprising:
a microprocessor, a special-purpose computer, or a general-purpose computer programmed for delivering specified volumes of reactants to the reaction chamber.

11. The reactor of claim 9, wherein one of the reactants comprises sodium chlorite.

12. The reactor of claim 9, wherein one of the reactants comprises sodium bisulfate, urea sulfate, or an organic acid blend.

13. The reactor of claim 1, wherein the first inlet pipe and the second inlet pipe are each configured to deliver specified volumes of reactants to the reaction chamber.

14. The reactor of claim 13, wherein one of the reactants is sodium chlorite.

15. The reactor of claim 13, wherein one of the reactants is selected from the group consisting of sodium bisulfate, urea sulfate and an organic acid blend, and is combined with sodium chlorite in the reaction chamber.

16. The reactor of claim 1, additionally comprising a separate pipe having an outlet downstream of said discharge valve in a flow of liquid receiving said chlorine dioxide from said discharge valve.

17. The reactor of claim 1, wherein the reactor releases chlorine dioxide in its gaseous phase via the pressure activated discharge valve.

18. A system for adding chlorine dioxide to a flow of liquid, comprising:
a reactor for generating chlorine dioxide, wherein the reactor comprises:

a reaction chamber defined by walls of a first piece and a second piece, the first piece having a threaded portion, and the second piece having a matingly threaded portion configured to couple to the threaded portion of the first piece, wherein the threaded portions of the first and second pieces are configured to adjust an interior volume of the reaction chamber by allowing adjustable positioning of the second piece within the threaded portion of the first piece;

a first inlet configured to accept a first reactant;

a second inlet configured to accept a second reactant; and an outlet, the outlet, the first inlet, and the second inlet each communicating with the reaction chamber, wherein the first piece and the second piece of the reactor are made of chemically resistant plastic, and at least a portion of the reactor is configured to be positioned within a pipe into which chlorine dioxide is to be released; and a microprocessor, a special-purpose computer, or a general-purpose computer appropriately programmed for delivering specified volumes of a reactant to the reaction chamber via the first inlet or the second inlet.

19. The system of claim 18, wherein the first reactant is sodium chlorite.

20. The system of claim 18, wherein the second reactant is selected from sodium bisulfate, urea sulfate and an organic acid blend, and is combined with sodium chlorite and sodium hypochlorite or hydrochlorous acid.

21. The system of claim 18, wherein the first reactant is selected from the group consisting of sodium bisulfate, urea sulfate and an organic acid blend, and the first reactant is combined with the second reactant comprising sodium chlorite in the reaction chamber.

22. A reactor for generating chlorine dioxide, comprising:

a reaction chamber defined by walls of a first piece and a second piece, the first piece having a threaded portion, and the second piece having a matingly threaded portion configured to couple to the threaded portion of the first piece, wherein the threaded portions of the first and second pieces are configured to adjust an interior volume of the reaction chamber by allowing adjustable positioning of said second piece within the threaded portion of the first piece;

a first inlet configured to accept a first reactant;

a second inlet configured to accept a second reactant; and an outlet, the outlet, the first inlet, and the second inlet each communicating with the reaction chamber, wherein the first piece and the second piece are made of chemically resistant plastic, and at least a portion of the reactor is configured to be positioned within a pipe into which chlorine dioxide is to be released.

23. The reactor of claim 22, wherein the outlet comprises an exit pipe coupled to a back flow check valve.

24. The reactor of claim 22, wherein the first piece and the second piece of the reactor comprise chlorinated polyvinyl chloride (CPVC) or polytetrafluoroethylene (PTFE), the first and second inlets are located on opposite sides of the reaction chamber from the outlet, and the reactor releases chlorine dioxide in its gaseous phase via the outlet.

* * * * *